United States Patent
Long et al.

(10) Patent No.: US 11,440,903 B2
(45) Date of Patent: Sep. 13, 2022

(54) SALT FORM AND CRYSTAL FORM OF COMPOUND AS FGFR4 INHIBITOR AND PREPARATION METHOD THEREOF

(71) Applicants: GUANGDONG ZHONGSHENG PHARMACEUTICAL CO., LTD, Guangdong (CN); GUANGDONG XIANQIANG PHARMACEUTICAL CO., LTD, Guangdong (CN)

(72) Inventors: Chaofeng Long, Guangdong (CN); Yang Zhang, Shanghai (CN); Zhengxia Chen, Shanghai (CN); Xiaoxin Chen, Guangdong (CN); Zhuowei Liu, Guangdong (CN); Meibi Dai, Shanghai (CN); Zhiqiang Liu, Guangdong (CN); Shuhui Chen, Shanghai (CN)

(73) Assignees: GUANGDONG ZHONGSHENG PHARMACEUTICAL CO., LTD, Guangdong (CN); GUANGDONG XIANQIANG PHARMACEUTICAL CO., LTD, Guangdong (CN)

(*) Notice: Subject to any disclaimer, the term of this patent is extended or adjusted under 35 U.S.C. 154(b) by 69 days.

(21) Appl. No.: 16/759,734

(22) PCT Filed: Oct. 30, 2018

(86) PCT No.: PCT/CN2018/112659
§ 371 (c)(1),
(2) Date: Apr. 28, 2020

(87) PCT Pub. No.: WO2019/085893
PCT Pub. Date: May 9, 2019

(65) Prior Publication Data
US 2021/0087181 A1    Mar. 25, 2021

(30) Foreign Application Priority Data
Nov. 1, 2017 (CN) .......................... 201711059786.4

(51) Int. Cl.
*C07D 405/12* (2006.01)

(52) U.S. Cl.
CPC ........ *C07D 405/12* (2013.01); *C07B 2200/13* (2013.01)

(58) Field of Classification Search
None
See application file for complete search history.

(56) References Cited

U.S. PATENT DOCUMENTS 11,008,292 B2 * 5/2021 Chen .................... C07D 403/12
2012/0245182 A1   9/2012 Berghausen
(Continued)

FOREIGN PATENT DOCUMENTS

| CN | 105061332 A | 11/2015 |
|----|-------------|---------|
| CN | 2017110597864 | 11/2017 |

(Continued)

OTHER PUBLICATIONS

Berkeley et al., Green Chemistry Letters and Review, 2009, 192-211.*

(Continued)

*Primary Examiner* — Clinton A Brooks
(74) *Attorney, Agent, or Firm* — Houston Beshining Law Office PLLC; Liangang Ye

(57) ABSTRACT

The present invention provides a salt form, a crystal form, and a preparation method of a compound as an FGFR4 inhibitor and medical uses thereof.

(I)

(Continued)

-continued

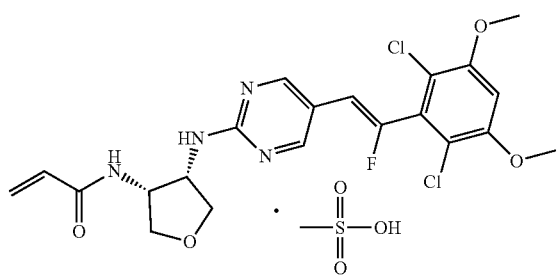

(II)

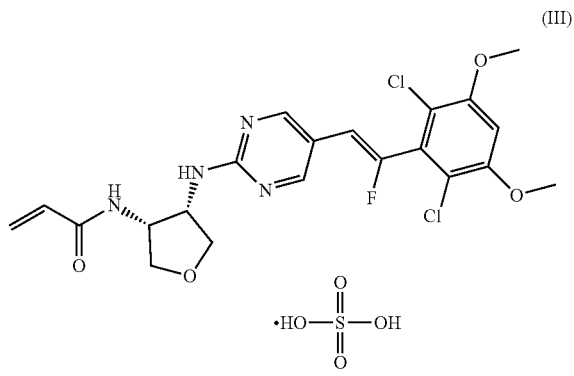

(III)

26 Claims, 11 Drawing Sheets

(56) References Cited

U.S. PATENT DOCUMENTS

2015/0119405 A1 4/2015 Bifulco, Jr. et al.
2020/0062716 A1 2/2020 Chen et al.

FOREIGN PATENT DOCUMENTS

| JP | 2016534059 A1 | 11/2016 |
| JP | 2019537613 A | 12/2019 |
| WO | 2016164703 A1 | 10/2016 |
| WO | 2018090973 A1 | 5/2018 |
| WO | 2818090973 A1 | 5/2018 |

OTHER PUBLICATIONS

Jan. 8, 2019 International Search Report issued in International Patent Application No. PCT/CN2018/112659.
Jan. 8, 2019 Written Opinion of the International Searching Authority issued in International Patent Application No. PCT/CN2018/112659.
Apr. 8, 2021 extended European search report issued in European Patent Application No. 18873402.4.
Apr. 27, 2021 Japanese Notice of Reasons for Refusal issued in Japanese Patent Application No. 2020-543682.
Wang Yikai et al: "Discovery and optimization of selective FGFR4 inhibitors via scaffold hopping", Biorganic IIE Medicinal Chemistry Letters, Elsevier, Amsterdam , NL, vol. 27, No. 11, Apr. 5, 2817 (Apr. 5, 2017), pp. 2428-2423.
Mo, Cheng, ACS Medicinal Chemistry Letters, 2017, and 8,543-548 and & Supp.Info. s1-s50 (especially compound 3a).
Nov. 2, 2021 2nd Office Action issued in Japanese Patent Application No. 2020-543682.

\* cited by examiner

SALT FORM AND CRYSTAL FORM OF COMPOUND AS FGFR4 INHIBITOR AND PREPARATION METHOD THEREOF

CROSS-REFERENCE TO RELATED APPLICATION

This application is a National Stage of International Application No. PCT/CN2018/112659, filed on Oct. 30, 2018, which claims the priority of the Chinese Patent Application No. CN201711059786.4, filed on Nov. 1, 2017, the contents of which are incorporated herein by reference in their entireties.

TECHNICAL FIELD

The present disclosure relates to salt forms and crystal forms of a class of compounds used as FGFR4 inhibitors, a preparation method thereof, and a medical use thereof.

BACKGROUND OF THE INVENTION

Fibroblast growth factor receptor 4 (FGFR4) is a kind of human protein encoded by the FGFR4 gene. This protein is a member of the fibroblast growth factor receptor family, and the homology of amino acid sequences among FGFR1-4 members is very high, with a high degree of similarity. The protein is a glycoprotein composed of an extracellular immunoglobulin (Ig)-like domain, a hydrophobic transmembrane domain and a cytoplasm portion including tyrosine kinase domain. The binding of the extramembrane domain to FGF leads to dimerization of FGFR, and the receptor undergoes autophosphorylation, thereby activating the downstream signal pathway, and finally affecting the division and variation of cells.

FGFR4 is distinctly different from FGFR1-3 in terms of genetic structure, FGFR4 has a specific structure of cysteine 552 (CYS552), thus being capable of selectively inhibiting FGFR4, rather than inhibiting the development of FGFR1-3 inhibitors, thereby reducing the potential toxicity caused by FGFR1-3 inhibition. It has been demonstrated from recent studies that FGFR4-FGF19 signal axes are closely related to liver cancer, renal cancer, colon cancer, breast cancer, etc., allowing FGFR4 to become one of the potential targets for treating liver cancer, renal cancer, colon cancer, breast cancer, etc.

In clinical applications, FGFR4 inhibitors are not limited to treatment of liver cancer with high expression of FGFR4, and may also be applied to other solid tumors with abnormal FGFR4 signal pathways, meanwhile, FGFR4 inhibitors may possibly be used in combination with other therapies. Therefore, the development of FGFR4 inhibitors has a rather extensive market space and application prospect.

SUMMARY OF THE INVENTION

For overcoming the disadvantages of the prior art, the present disclosure provides a salt form of compound as FGFR4 inhibitor, and a series of crystal forms corresponding to the salt form and free base thereof, thereby providing a plurality of candidate raw materials for the development of the FGFR4 inhibitor as clinical medicament.

For the characterization of the crystal form of a compound, those skilled in the art can understand that, for a specific crystal form of a specific compound, the 2θ angles of the respective diffraction peaks in the X-ray powder diffraction pattern thereof will deviate in duplicate trials due to the influence of equipment, operation method, sample purity, and human factors, and the deviation range (error range) is generally within ±0.2°; moreover, those skilled in the art can further understand that the stability and repeatability of the diffraction peaks will be influenced by a combination of 2θ angles, absorption intensities of the respective diffraction peaks of the X-ray powder diffraction pattern, and the like; in particular, the diffraction peaks with stronger absorption intensity, better separation and smaller 2θ angle have better stability and repeatability, and have greater possibility in characterizing the specific crystal form; as to the diffraction peaks with larger 2θ angles and/or poorer separation and/or weaker relative intensity, relatively greater fluctuation is likely to occur due to the influences of instrument equipment, operation methods, sample purity, human factors, and the like, or those diffraction peaks may not repeatedly appear in repeated trials, therefore, for those skilled in the art, such absorption peaks are not essential diffraction peaks for characterizing the crystal form. More specially, the larger 2θ angle described herein refers to the 2θ≥30°, and the peak with weaker absorption intensity refers to that its relative intensity is less than 10%.

The first object of the present disclosure is to provide a crystal form A of the compound represented by formula (I), wherein the X-ray powder diffraction pattern thereof has the most stable and repeatable characteristic diffraction peaks at the following 2θ angles: 5.58±0.2°, 21.31±0.2°, 22.97±0.2°.

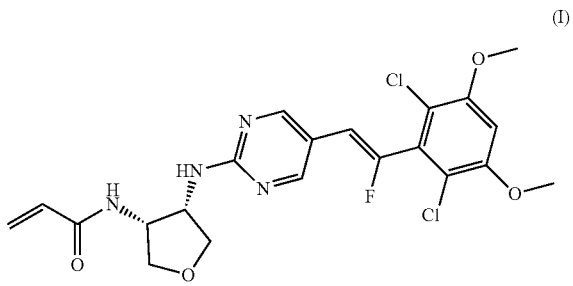 [SMILES: C=CC(=O)N[C@H]1COC[C@H]1Nc1ncc(/C=C(\F)c2c(Cl)c(OC)cc(OC)c2Cl)cn1]

(I)

Further, in some embodiments of the present disclosure, the X-ray powder diffraction pattern of the crystal form A has secondarily stable and repeatable characteristic diffraction peaks at the following 2θ angles: 5.58±0.2°, 12.43±0.2°, 14.56±0.2°, 18.47±0.2°, 20.23±0.2°, 21.31±0.2°, 22.97±0.2°, 25.44±0.2°.

Further, in some embodiments of the present disclosure, the X-ray powder diffraction pattern of the crystal form A has secondarily stable and repeatable characteristic diffraction peaks at the following 2θ angles: 5.58±0.2°, 12.43±0.2°, 12.77±0.2°, 13.00±0.2°, 14.56±0.2°, 18.47±0.2°, 20.23±0.2°, 21.00±0.2°, 21.31±0.2°, 22.44±0.2°, 22.97±0.2°, 24.86±0.2°, 25.44±0.2°, 27.14±0.2°.

Further, in an embodiment of the present disclosure, the analytical data of the XRPD pattern of the crystal form A are as shown in Table 1:

TABLE 1

XRPD Analytical Data of the Crystal Form A of the Compound Represented by Formula (I)

| Number | 2θ Angle (°) | d-Spacing (Å) | Relative Intensity (%) |
|---|---|---|---|
| 1 | 5.583 | 15.8165 | 7.9 |
| 2 | 10.946 | 8.0763 | 7.6 |
| 3 | 11.512 | 7.6803 | 5.1 |
| 4 | 12.427 | 7.117 | 21.3 |
| 5 | 12.765 | 6.9292 | 24.5 |
| 6 | 13 | 6.8045 | 46 |
| 7 | 14.562 | 6.0779 | 10.2 |
| 8 | 15.691 | 5.6431 | 5.1 |
| 9 | 16.66 | 5.3169 | 7.5 |
| 10 | 17.96 | 4.9348 | 6.7 |
| 11 | 18.47 | 4.7998 | 24.3 |
| 12 | 19.598 | 4.5259 | 6 |
| 13 | 20.229 | 4.3862 | 29 |
| 14 | 20.999 | 4.2271 | 13.2 |
| 15 | 21.311 | 4.1658 | 47.9 |
| 16 | 22.44 | 3.9587 | 13 |
| 17 | 22.973 | 3.8682 | 100 |
| 18 | 24.864 | 3.578 | 16.5 |
| 19 | 25.438 | 3.4986 | 59.4 |
| 20 | 27.136 | 3.2834 | 12.5 |
| 21 | 27.607 | 3.2284 | 8.4 |
| 22 | 27.871 | 3.1985 | 6.1 |
| 23 | 28.818 | 3.0955 | 7.3 |
| 24 | 29.447 | 3.0308 | 5.9 |
| 25 | 31.343 | 2.8516 | 3.8 |
| 26 | 31.788 | 2.8127 | 3.9 |
| 27 | 32.247 | 2.7737 | 4.3 |
| 28 | 32.584 | 2.7458 | 11.3 |

Further, in an embodiment of the present disclosure, the XRPD pattern of the crystal form A is as shown in FIG. 1.

In some embodiments of the present disclosure, the differential scanning calorimetric curve of the crystal form A has an endothermic peak with an onset of 174.46° C.±3° C.

Furthermore, in an embodiment of the present disclosure, the DSC pattern of the crystal form A is as shown in FIG. 2.

In some embodiments of the present disclosure, the thermogravimetric analysis curve of the crystal form A has a weight loss of 0.02335% occurred at 120.00° C.±3° C. and an additional weight loss of 0.2869% occurred at 200.85° C.±3° C.

Further, in an embodiment of the present disclosure, the TGA pattern of the crystal form A is as shown in FIG. 3.

The second object of the present disclosure is to provide a crystal form B of the compound represented by formula (I), wherein the X-ray powder diffraction pattern thereof has the most stable and repeatable characteristic diffraction peaks at the following 2θ angles: 9.27±0.2°, 12.59±0.2°, 15.98±0.2°.

Further, in some embodiments of the present disclosure, the X-ray powder diffraction pattern of the crystal form B has secondarily stable and repeatable characteristic diffraction peaks at the following 2θ angles: 9.27±0.2°, 12.59±0.2°, 15.21±0.2°, 15.98±0.2°, 18.47±0.2°, 20.90±0.2°, 21.79±0.2°, 27.69±0.2°.

Further, in some embodiments of the present disclosure, the X-ray powder diffraction pattern of the crystal form B has secondarily stable and repeatable characteristic diffraction peaks at the following 2θ angles: 9.27±0.2°, 12.12±0.2°, 12.59±0.2°, 15.21±0.2°, 15.98±0.2°, 18.47±0.2°, 20.90±0.2°, 21.79±0.2°, 22.60±0.2°, 22.85±0.2°, 24.16±0.2°, 24.39±0.2°, 27.69±0.2°.

Further, in an embodiment of the present disclosure, the analytical data of the XRPD pattern of the crystal form B are as shown in Table 2:

TABLE 2

XRPD Analytical Data of the Crystal Form B of the Compound Represented by Formula (I)

| Number | 2θ Angle (°) | d-Spacing (Å) | Relative Intensity (%) |
|---|---|---|---|
| 1 | 6.149 | 14.3616 | 7.6 |
| 2 | 7.044 | 12.5387 | 2.2 |
| 3 | 9.272 | 9.5304 | 66.2 |
| 4 | 12.115 | 7.2994 | 13 |
| 5 | 12.587 | 7.0265 | 100 |
| 6 | 13.97 | 6.334 | 7 |
| 7 | 15.212 | 5.8196 | 9.3 |
| 8 | 15.982 | 5.541 | 21.4 |
| 9 | 18.468 | 4.8003 | 15.3 |
| 10 | 19.383 | 4.5756 | 5.4 |
| 11 | 19.713 | 4.4997 | 9.9 |
| 12 | 20.01 | 4.4336 | 5.7 |
| 13 | 20.9 | 4.2468 | 56.3 |
| 14 | 21.508 | 4.1281 | 9.3 |
| 15 | 21.785 | 4.0762 | 33.2 |
| 16 | 22.302 | 3.9829 | 5.1 |
| 17 | 22.596 | 3.9318 | 12.7 |
| 18 | 22.853 | 3.8881 | 11.1 |
| 19 | 23.404 | 3.7979 | 7 |
| 20 | 24.156 | 3.6812 | 26.6 |
| 21 | 24.394 | 3.6459 | 28.7 |
| 22 | 24.685 | 3.6035 | 8.4 |
| 23 | 25.182 | 3.5336 | 7.4 |
| 24 | 26.365 | 3.3776 | 8.6 |
| 25 | 27.693 | 3.2186 | 24.1 |
| 26 | 28.777 | 3.0997 | 6.8 |
| 27 | 29.856 | 2.9901 | 3.2 |
| 28 | 31.482 | 2.8393 | 5.4 |
| 29 | 32.096 | 2.7864 | 1.4 |
| 30 | 33.435 | 2.6778 | 7.4 |
| 31 | 35.627 | 2.5179 | 3.4 |
| 32 | 36.515 | 2.4587 | 4.3 |
| 33 | 37.027 | 2.4259 | 5.5 |
| 34 | 38.018 | 2.3649 | 4.3 |

Further, in an embodiment of the present disclosure, the XRPD pattern of the crystal form B is as shown in FIG. 4.

In some embodiments of the present disclosure, the differential scanning calorimetric curve of the crystal form B has an endothermic peak with an onset of 178.04° C.±3° C.

Further, in an embodiment of the present disclosure, the DSC pattern of the crystal form B is as shown in FIG. 5.

In some embodiment of the present disclosure, the thermogravimetric analysis curve of the crystal form B has a weight loss of 0.8093% occurred at 120.00° C.±3° C., and an additional weight loss of 1.128% occurred at 200.04° C.±3° C.

Further, in an embodiment of the present disclosure, the TGA pattern of the crystal form B is as shown in FIG. 6.

The third object of the present disclosure is to provide a crystal form C of the compound represented by formula (I), wherein the X-ray powder diffraction pattern thereof has the most stable and repeatable characteristic diffraction peaks at the following 2θ angles: 4.35±0.2°, 10.50±0.2°, 12.25±0.2°.

Further, in some embodiments of the present disclosure, the X-ray powder diffraction pattern of the crystal form C has secondarily stable and repeatable characteristic diffraction peaks at the following 2θ angles: 4.35±0.2°, 8.38±0.2°, 10.50±0.2°, 12.25±0.2°, 12.82±0.2°, 13.45±0.2°, 16.36±0.2°, 18.65±0.2°.

Further, in some embodiments of the present disclosure, the X-ray powder diffraction pattern of the crystal form C has secondarily stable and repeatable characteristic diffraction peaks at the following 2θ angles: 4.35±0.2°, 8.38±0.2°, 10.50±0.2°, 11.84±0.2°, 12.25±0.2°, 12.82±0.2°, 13.45±0.2°, 16.36±0.2°, 16.64±0.2°, 17.05±0.2°, 17.92±0.2°, 18.65±0.2°, 19.79±0.2°, 20.21±0.2°, 20.52±0.2°, 21.19±0.2°, 22.18±0.2°, 23.23±0.2°, 23.84±0.2°, 24.65±0.2°, 25.67±0.2°, 26.17±0.2°, 28.91±0.2°.

Further, in an embodiment of the present disclosure, the analytical data of the XRPD pattern of the crystal form C are as shown in Table 3:

TABLE 3

XRPD Analytic Data of the Crystal Form C of the Compound Represented by Formula (I)

| Number | 2θ Angle (°) | d-Spacing (Å) | Relative Intensity (%) |
|---|---|---|---|
| 1 | 4.352 | 20.2853 | 13.6 |
| 2 | 8.378 | 10.5446 | 15.3 |
| 3 | 10.496 | 8.4216 | 25.7 |
| 4 | 11.838 | 7.4697 | 72.1 |
| 5 | 12.253 | 7.2178 | 100 |
| 6 | 12.824 | 6.8974 | 29.9 |
| 7 | 13.453 | 6.5765 | 18.3 |
| 8 | 14.131 | 6.2622 | 7.7 |
| 9 | 16.359 | 5.4141 | 15.1 |
| 10 | 16.637 | 5.324 | 11 |
| 11 | 17.047 | 5.197 | 19.9 |
| 12 | 17.685 | 5.011 | 8.5 |
| 13 | 17.92 | 4.9458 | 13 |
| 14 | 18.647 | 4.7545 | 28.2 |
| 15 | 19.006 | 4.6656 | 4.4 |
| 16 | 19.419 | 4.5673 | 6.8 |
| 17 | 19.789 | 4.4827 | 12 |
| 18 | 20.207 | 4.3909 | 26.6 |
| 19 | 20.522 | 4.3241 | 33.9 |
| 20 | 20.979 | 4.231 | 9.2 |
| 21 | 21.194 | 4.1885 | 17 |
| 22 | 21.628 | 4.1054 | 6 |
| 23 | 22.181 | 4.0043 | 14.2 |
| 24 | 22.578 | 3.9349 | 3.2 |
| 25 | 23.231 | 3.8257 | 10 |
| 26 | 23.838 | 3.7296 | 22.9 |
| 27 | 24.65 | 3.6086 | 21.2 |
| 28 | 24.984 | 3.5611 | 10.5 |
| 29 | 25.673 | 3.4671 | 16.2 |
| 30 | 26.169 | 3.4025 | 19.1 |
| 31 | 26.465 | 3.3651 | 9.5 |
| 32 | 27.158 | 3.2808 | 5.5 |
| 33 | 27.602 | 3.229 | 4.6 |
| 34 | 28.025 | 3.1813 | 9.4 |
| 35 | 28.679 | 3.1102 | 11.5 |
| 36 | 28.914 | 3.0853 | 13.3 |
| 37 | 30.629 | 2.9164 | 5.3 |
| 38 | 31.052 | 2.8776 | 8.5 |
| 39 | 32.705 | 2.7359 | 5.7 |
| 40 | 35.821 | 2.5048 | 10.3 |

Further, in an embodiment of the present disclosure, the XRPD pattern of the crystal form C is as shown in FIG. 7.

In some embodiments of the present disclosure, the differential scanning calorimetric curve of the crystal form C has an endothermic peak with an onset of 179.19° C.±3° C.

Further, in an embodiment of the present disclosure, the DSC pattern of the crystal form C is as shown in FIG. 8.

In some embodiments of the present disclosure, the thermogravimetric analysis curve of the crystal form C has a weight loss of 0.4101% occurred at 120.00° C.±3° C., and an additional weight loss of 0.2938% occurred at 200.31° C.±3° C.

Further, in an embodiment of the present disclosure, the TGA pattern of the crystal form C is as shown in FIG. 9.

The fourth object of the present disclosure is to provide a crystal form D of the compound represented by formula (I), wherein the X-ray powder diffraction pattern thereof has the most stable and repeatable characteristic diffraction peaks at the following 2θ angles: 5.68±0.2°, 14.68±0.2°, 23.05±0.2°.

Further, in some embodiments of the present disclosure, the X-ray powder diffraction pattern of the crystal form D has secondarily stable and repeatable characteristic diffraction peaks at the following 2θ angles: 5.68±0.2°, 12.53±0.2°, 14.68±0.2°, 18.55±0.2°, 20.33±0.2°, 21.41±0.2°, 23.05±0.2°, 25.52±0.2°.

Further, in some embodiments of the present disclosure, the X-ray powder diffraction pattern of the crystal form D has secondarily stable and repeatable characteristic diffraction peaks at the following 2θ angles: 5.68±0.2°, 12.53±0.2°, 13.06±0.2°, 14.68±0.2°, 16.81±0.2°, 18.55±0.2°, 20.33±0.2°, 20.98±0.2°, 21.41±0.2°, 22.58±0.2°, 23.05±0.2°, 24.96±0.2°, 25.52±0.2°, 27.25±0.2°.

Further, in an embodiment of the present disclosure, the analytical data of the XRPD pattern of the crystal form D are as shown in Table 4:

TABLE 4

XRPD Analytical Data of the Crystal Form D of the Compound Represented by Formula (I)

| Number | 2θ Angle (°) | d-Spacing (Å) | Relative Intensity (%) |
|---|---|---|---|
| 1 | 5.679 | 15.5486 | 11.7 |
| 2 | 11.008 | 8.0305 | 9.5 |
| 3 | 11.559 | 7.6492 | 4.8 |
| 4 | 12.527 | 7.0605 | 31.8 |
| 5 | 12.864 | 6.8762 | 32.4 |
| 6 | 13.061 | 6.7726 | 53.2 |
| 7 | 14.679 | 6.0296 | 14.5 |
| 8 | 15.786 | 5.6092 | 6 |
| 9 | 16.809 | 5.2701 | 10.3 |
| 10 | 18.076 | 4.9035 | 9.2 |
| 11 | 18.549 | 4.7795 | 32.7 |
| 12 | 19.657 | 4.5125 | 6.5 |
| 13 | 20.325 | 4.3657 | 37 |
| 14 | 20.979 | 4.231 | 18.3 |
| 15 | 21.409 | 4.1471 | 55.2 |
| 16 | 22.281 | 3.9866 | 5.4 |
| 17 | 22.575 | 3.9354 | 19 |
| 18 | 23.049 | 3.8555 | 100 |
| 19 | 24.964 | 3.5639 | 22.4 |
| 20 | 25.517 | 3.488 | 67.4 |
| 21 | 26.097 | 3.4117 | 3.6 |
| 22 | 26.41 | 3.372 | 4.6 |
| 23 | 27.254 | 3.2694 | 19.1 |
| 24 | 27.65 | 3.2235 | 8.9 |
| 25 | 27.981 | 3.1861 | 7.5 |
| 26 | 28.895 | 3.0874 | 9.7 |
| 27 | 29.544 | 3.021 | 7 |
| 28 | 31.775 | 2.8138 | 5.6 |
| 29 | 32.643 | 2.7409 | 16 |
| 30 | 33.692 | 2.6579 | 5.7 |
| 31 | 34.383 | 2.6061 | 4.3 |
| 32 | 34.737 | 2.5804 | 5.5 |
| 33 | 36.87 | 2.4358 | 5.3 |
| 34 | 37.936 | 2.3698 | 5.6 |
| 35 | 38.601 | 2.3305 | 4.6 |

Further, in an embodiment of the present disclosure, the XRPD pattern of the crystal form D is as shown in FIG. 10.

In some embodiments of the present disclosure, the differential scanning calorimetric curve of the crystal form D has an endothermic peak with an onset of 179.17° C.±3° C.

Further, in an embodiment of the present disclosure, the DSC pattern of the crystal form D is as shown in FIG. 11.

In some embodiments of the present disclosure, the thermogravimetric analysis curve of the crystal form D has a weight loss of 0.6366% at 196.80° C.±3° C.

Further, in an embodiment of the present disclosure, the TGA pattern of the crystal form D is as shown in FIG. 12.

The fifth object of the present disclosure is to provide a compound represented by formula (II)

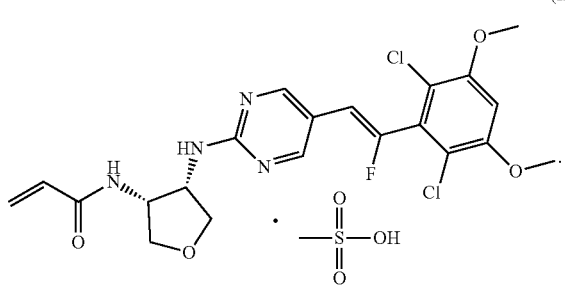

(II)

Researchers have found through solubility experiments that the compound represented by formula (II) has a relatively good solubility in a simulated gastric fluid (SGF) and in fasting or satiety state simulated intestinal fluid (FaSSIF). Therefore, the compound represented by formula (II) has a prospect to be developed as medicaments.

The sixth object of the present disclosure is to provide a crystal form E of the compound represented by formula (II), wherein the X-ray powder diffraction pattern thereof has the most stable and repeatable characteristic diffraction peaks at the following 2θ angles: 5.95±0.2°, 11.77±0.2°, 22.42±0.2°.

Further, in some embodiments of the present disclosure, the X-ray powder diffraction pattern of the crystal form E has secondarily stable and repeatable characteristic diffraction peaks at the following 2θ angles: 5.95±0.2°, 11.77±0.2°, 12.53±0.2°, 18.53±0.2°, 19.28±0.2°, 21.12±0.2°, 22.42±0.2°, 25.76±0.2°.

Further, in some embodiments of the present disclosure, the X-ray powder diffraction pattern of the crystal form E has secondarily stable and repeatable characteristic diffraction peaks at the following 2θ angles: 5.95±0.2°, 11.77±0.2°, 11.98±0.2°, 12.53±0.2°, 18.53±0.2°, 19.28±0.2°, 20.78±0.2°, 21.12±0.2°, 21.50±0.2°, 21.99±0.2°, 22.42±0.2°, 23.01±0.2°, 23.94±0.2°, 24.35±0.2°, 25.06±0.2°, 25.76±0.2°, 27.12±0.2°.

Further, in an embodiment of the present disclosure, the analytical data of the XRPD pattern of the crystal form E are as shown in Table 5:

TABLE 5

XRPD Analytical Data of the Crystal Form E of the Compound Represented by Formula (II)

| Number | 2θ Angle (°) | d-Spacing (Å) | Relative Intensity (%) |
|---|---|---|---|
| 1 | 5.95 | 14.8406 | 48.3 |
| 2 | 10.752 | 8.2215 | 3.8 |
| 3 | 11.772 | 7.5112 | 42.8 |
| 4 | 11.978 | 7.3828 | 19.5 |
| 5 | 12.529 | 7.0591 | 36.9 |
| 6 | 17.599 | 5.0353 | 4.1 |
| 7 | 18.528 | 4.7847 | 27.8 |
| 8 | 19.281 | 4.5996 | 27.1 |
| 9 | 20.111 | 4.4117 | 6.6 |
| 10 | 20.445 | 4.3403 | 4.2 |
| 11 | 20.781 | 4.271 | 24 |
| 12 | 21.115 | 4.204 | 59.7 |
| 13 | 21.495 | 4.1307 | 20.7 |
| 14 | 21.985 | 4.0397 | 15.5 |
| 15 | 22.418 | 3.9627 | 100 |
| 16 | 23.01 | 3.8619 | 18.4 |
| 17 | 23.942 | 3.7137 | 18.6 |
| 18 | 24.353 | 3.6519 | 33 |
| 19 | 25.063 | 3.55 | 15.2 |
| 20 | 25.303 | 3.517 | 6.9 |
| 21 | 25.756 | 3.4561 | 29.2 |
| 22 | 26.073 | 3.4148 | 7.1 |
| 23 | 26.368 | 3.3772 | 9 |
| 24 | 26.681 | 3.3383 | 11 |
| 25 | 27.116 | 3.2857 | 14.4 |
| 26 | 28.653 | 3.1129 | 8.7 |
| 27 | 29.423 | 3.0332 | 2.4 |
| 28 | 30.023 | 2.9739 | 11.4 |
| 29 | 30.828 | 2.8981 | 10.6 |
| 30 | 31.341 | 2.8518 | 17.4 |
| 31 | 31.933 | 2.8002 | 9 |
| 32 | 32.464 | 2.7556 | 6.4 |
| 33 | 32.841 | 2.7248 | 4.7 |
| 34 | 33.315 | 2.6872 | 4.9 |
| 35 | 34.974 | 2.5634 | 27.3 |
| 36 | 37.639 | 2.3878 | 7.6 |

Further, in an embodiment of the present disclosure, the XRPD pattern of the crystal form E is as shown in FIG. 13.

In some embodiments of the present disclosure, the differential scanning calorimetric curve of the crystal form E has an endothermic peak with an onset of 193.78° C.±3° C. and an exothermic peak at 198.70° C.±3° C.

Further, in an embodiment of the present disclosure, the DSC pattern of the crystal form E is as shown in FIG. 14.

In some embodiments of the present disclosure, the thermogravimetric analysis curve of the crystal form E has a TGA curve with a weight loss of 1.086% occurred at 170.64° C.±3° C. and an additional weight loss of 1.652% occurred at 210.29° C.±3° C.

Further, in an embodiment of the present disclosure, the TGA pattern of the crystal form E is as shown in FIG. 15.

The seventh object of the present disclosure is to provide a crystal form F of the compound represented by formula (II), wherein the X-ray powder diffraction pattern thereof has the most stable and repeatable characteristic diffraction peaks at the following 2θ angles: 6.04±0.2°, 9.21±0.2°, 12.51±0.2°.

Further, in some embodiments of the present disclosure, the X-ray powder diffraction pattern of the crystal form F has secondarily stable and repeatable characteristic diffraction peaks at the following 2θ angles: 6.04±0.2°, 9.21±0.2°, 12.02±0.2°, 12.51±0.2°, 15.89±0.2°, 18.35±0.2°, 20.84±0.2°, 21.67±0.2°.

Further, in some embodiments of the present disclosure, the X-ray powder diffraction pattern of the crystal form F has secondarily stable and repeatable characteristic diffraction peaks at the following 2θ angles: 6.04±0.2°, 9.21±0.2°, 12.02±0.2°, 12.51±0.2°, 15.89±0.2°, 18.35±0.2°, 19.71±0.2°, 20.84±0.2°, 21.67±0.2°, 22.59±0.2°, 24.14±0.2°, 27.64±0.2°.

Further, in an embodiment of the present disclosure, the analytical data of the XRPD pattern of the crystal form F are as shown in Table 6:

TABLE 6

XRPD Analytical Data of Crystal Form F of the Compound Represented by Formula (II)

| Number | 2θ Angle (°) | d-Spacing (Å) | Relative Intensity (%) |
|---|---|---|---|
| 1 | 6.036 | 14.6291 | 19.8 |
| 2 | 9.209 | 9.5948 | 100 |
| 3 | 12.017 | 7.3589 | 17 |
| 4 | 12.509 | 7.0705 | 98.6 |
| 5 | 13.889 | 6.3709 | 7.9 |
| 6 | 15.114 | 5.8572 | 9.1 |
| 7 | 15.885 | 5.5745 | 22.1 |
| 8 | 18.352 | 4.8302 | 15.2 |
| 9 | 19.286 | 4.5984 | 4 |
| 10 | 19.71 | 4.5004 | 12.6 |
| 11 | 20.027 | 4.43 | 7.2 |
| 12 | 20.839 | 4.2592 | 51.1 |
| 13 | 21.669 | 4.0977 | 32.7 |
| 14 | 22.324 | 3.9791 | 5.9 |
| 15 | 22.594 | 3.9321 | 14.7 |
| 16 | 23.348 | 3.8069 | 7.6 |
| 17 | 24.136 | 3.6842 | 28.5 |
| 18 | 24.647 | 3.609 | 9.3 |
| 19 | 25.048 | 3.5522 | 4.5 |
| 20 | 26.288 | 3.3873 | 7.3 |
| 21 | 27.136 | 3.2834 | 4 |
| 22 | 27.649 | 3.2236 | 18.3 |
| 23 | 28.481 | 3.1313 | 4.1 |
| 24 | 28.831 | 3.0941 | 6.2 |
| 25 | 29.781 | 2.9975 | 3.2 |
| 26 | 31.479 | 2.8396 | 4.9 |
| 27 | 33.354 | 2.6841 | 5.9 |
| 28 | 33.588 | 2.6659 | 4.8 |
| 29 | 36.511 | 2.4589 | 4.7 |
| 30 | 36.944 | 2.4311 | 4.2 |
| 31 | 37.953 | 2.3688 | 2.8 |

Further, in an embodiment of the present disclosure, the XRPD pattern of the crystal form F is as shown in FIG. 16.

In some embodiments of the present disclosure, the differential scanning calorimetric curve of the crystal form F has an endothermic peak with an onset of 155.72° C.±3° C.

Further, in an embodiment of the present disclosure, the DSC pattern of the crystal form F is as shown in FIG. 17.

In some embodiments of the present disclosure, the TGA curve of the crystal form F has a weight loss of 0.6525% occurred at 120° C.±3° C., and an additional weight loss of 1.138% occurred at 205.16° C.±3° C.

Further, in an embodiment of the present disclosure, the TGA pattern of the crystal form F is as shown in FIG. 18.

The eighth object of the present disclosure is to provide a compound represented by formula (III)

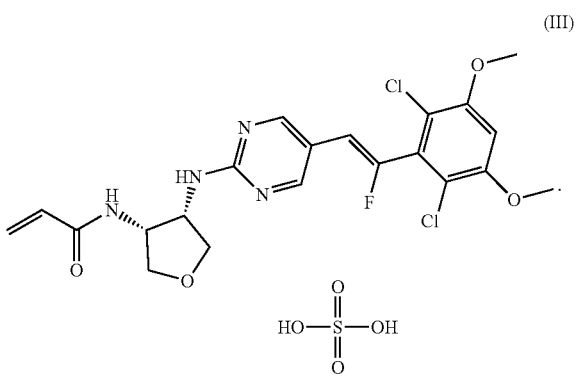 [SMILES: C=CC(=O)N[C@H]1COC[C@H]1Nc1ncc(/C=C(\F)c2c(Cl)c(OC)cc(OC)c2Cl)cn1 ; O=S(=O)(O)O]

(III)

Researchers have found through solubility experiments that the compound represented by formula (III) also has a relatively good solubility in a simulated gastric fluid (SGF) and in fasting or satiety state simulated intestinal fluid (FaSSIF). Therefore, the compound represented by formula (III) also has a prospect to be developed as medicaments.

The ninth object of the present disclosure is to provide a crystal form G of the compound represented by formula (III), wherein the X-ray powder diffraction pattern thereof has the most stable and repeatable characteristic diffraction peaks at the following 2θ angles: 5.86±0.2°, 11.62±0.2°, 22.81±0.2°.

Further, in some embodiments of the present disclosure, the X-ray powder diffraction pattern of the crystal form G has secondarily stable and repeatable characteristic diffraction peaks at the following 2θ angles: 5.86±0.2°, 11.62±0.2°, 12.31±0.2°, 19.22±0.2°, 20.03±0.2°, 22.81±0.2°, 23.68±0.2°, 24.75±0.2°.

Further, in some embodiments of the present disclosure, the X-ray powder diffraction pattern of the crystal form G has secondarily stable and repeatable characteristic diffraction peaks at the following 2θ angles: 5.86±0.2°, 11.62±0.2°, 12.31±0.2°, 19.22±0.2°, 20.03±0.2°, 20.84±0.2°, 21.18±0.2°, 21.63±0.2°, 22.81±0.2°, 23.68±0.2°, 24.75±0.2°, 26.23±0.2°, 26.82±0.2°.

Further, in an embodiment of the present disclosure, the analytical data of the XRPD pattern of the crystal form G are as shown in Table 7:

TABLE 7

XRPD Analytic Data of Crystal Form G of the Compound Represented by Formula (III)

| Number | 2θ Angle (°) | d-Spacing (Å) | Relative Intensity (%) |
|---|---|---|---|
| 1 | 5.857 | 15.0769 | 30.6 |
| 2 | 10.558 | 8.3719 | 6.1 |
| 3 | 11.624 | 7.6067 | 37.4 |
| 4 | 12.31 | 7.1843 | 22.8 |
| 5 | 19.22 | 4.6141 | 33 |
| 6 | 20.028 | 4.4297 | 26.3 |
| 7 | 20.839 | 4.2591 | 43.6 |
| 8 | 21.175 | 4.1923 | 22.3 |
| 9 | 21.63 | 4.1051 | 14.4 |
| 10 | 22.186 | 4.0036 | 4.7 |
| 11 | 22.812 | 3.8951 | 100 |
| 12 | 23.682 | 3.7538 | 30.6 |
| 13 | 24.746 | 3.5948 | 53.3 |
| 14 | 25.175 | 3.5345 | 6.6 |
| 15 | 26.229 | 3.3948 | 26.9 |
| 16 | 26.821 | 3.3212 | 17.5 |
| 17 | 27.333 | 3.2601 | 5.5 |
| 18 | 28.968 | 3.0797 | 8.5 |
| 19 | 29.168 | 3.0591 | 4.5 |
| 20 | 30.298 | 2.9475 | 10.6 |
| 21 | 30.612 | 2.918 | 9.1 |
| 22 | 31.599 | 2.8291 | 17.2 |
| 23 | 31.868 | 2.8058 | 6.9 |
| 24 | 32.707 | 2.7358 | 3.6 |
| 25 | 35.15 | 2.551 | 19.5 |
| 26 | 37.897 | 2.3721 | 5.3 |
| 27 | 38.823 | 2.3177 | 7.9 |

Further, in an embodiment of the present disclosure, the XRPD pattern of the crystal form G is as shown in FIG. 19.

In some embodiments of the present disclosure, the differential scanning calorimetric curve of the crystal form G has an endothermic peak at 164.93° C.±3° C.

Further, in an embodiment of the present disclosure, the DSC pattern of the crystal form G is as shown in FIG. 20.

In some embodiments of the present disclosure, the thermogravimetric analysis curve of the crystal form G has a weight loss of 0.2051% occurred at 120° C.±3° C., and an additional weight loss of 2.867% occurred at 218.92° C.±3° C.

Further, in an embodiment of the present disclosure, the TGA pattern of the crystal form G is as shown in FIG. 21.

The last object of the present disclosure is to further provide a method for preparing a crystal form B of the compound represented by formula (I), comprising preparing the crystal form B by adding the compound represented by formula (I) into a solvent, heating and stirring, or by carrying out recrystallization.

In some embodiments of the present disclosure, in the preparation method, the solvent is selected from: methanol, ethanol, acetone, tetrahydrofuran, isopropanol or ethanol-water.

In some embodiments of the present disclosure, in the preparation method, the stirring temperature is selected to be 10° C. to 45° C.

In some embodiments of the present disclosure, in the preparation method, the slurrying time is 10 hours to 60 hours.

In some embodiments of the present disclosure, in the preparation method, the weight-volume ratio of the compound to the solvent is 1:8-15 g/mL.

The present disclosure further provides the use of the compounds or the crystal forms A-G in the manufacture of a medicament for treating FGFR4 related disease.

Definition and Description

Unless otherwise stated, the following terms and phrases used herein are intended to have the following meanings. A specific phrase or term without specific definition should not be considered uncertain or unclear, but should be understood in line with its ordinary meaning. When a trade name is used herein, it is intended to refer to the corresponding commercially available product or its active ingredient(s).

The intermediate compound(s) of the present disclosure can be prepared by a variety of synthetic methods well known by those skilled in the art, including the specific embodiments as listed below, the embodiments formed by a combination of those embodiments with other chemical synthesis methods, as well as equivalent alternatives well known by those skilled in the art. Preferred embodiments include, but are not limited to, the embodiments of the present disclosure.

The chemical reaction(s) of the specific embodiments of the present disclosure is carried out in a suitable solvent which should be suitable for the chemical changes of the present disclosure and the required reagents and materials. In order to obtain the compounds of the present disclosure, those skilled in the art sometimes need to modify or make selection on the synthesis steps or the reaction process based on the existing embodiments.

Hereinafter the present disclosure will be described in details by reference to the embodiments which do not indicate any limitation to the present disclosure.

All the solvents used in the present disclosure are commercially available, and can be used without further purification.

The following abbreviations are used in the present disclosure: r.t. represents room temperature; THF represents tetrahydrofuran; NMP represents N-methylpyrrolidone; MeSO$_3$H represents methanesulfonic acid; DME represents 1,2-dimethoxyethane; DCM represents dichloromethane; Xphos represents 2-dicyclohexylphosphino-2'4'6'-tri-isopropylbiphenyl; EtOAc represents ethyl acetate; MeOH represents methanol; acetone represents propanone; 2-Me-THF represents 2-methyltetrahydrofuran; IPA represents isopropanol; m-CPBA represents 3-chloroperoxybenzoic acid; Pd(dppf)Cl$_2$ represents [1,1'-bis(diphenylphosphino)ferrocene]palladium dichloride; DIEA represents N,N-diisopropylethylamine; DMSO represents dimethylsulfoxide; HEPES represents 4-hydroxyethylpiperazine ethanesulfonic acid; and EGTA represents ethylene glycol bis(2-aminoethyl ether) tetraacetic acid.

Compounds are named manually or by ChemDraw® software, and commercially available compounds are named with supplier catalog names.

X-Ray Powder Diffractometer (XRPD) Method of the Present Invention

Instrument model: Bruker D8 advance X-ray diffractometer

Test method: About 10-20 mg sample was used for XRPD detection.

The detailed XRPD parameters are as follows:

X-ray tube: Cu, kα, (λ=1.54056Å).
X-ray tube voltage: 40 kV, X-ray tube current: 40 mA
Divergence slit: 0.60 mm
Detector slit: 10.50 mm
Anti-scattering slit: 7.10 mm
Scan range: 4-40 deg
Step size: 0.02 deg
Step length: 0.12 second
Rotation speed of sample tray: 15 rpm Those skilled in the art can understand that, during the analysis process of the obtained XRPD pattern, the relevant data can be subjected to appropriate scientific processing, such as baseline correction processing, in order to reduce errors.

Differential Scanning Calorimeter (DSC) Method of the Present Invention

Instrument model: TA Q2000 Differential Scanning calorimeter

Test method: A sample (about 1 mg) was placed into a DSC aluminum crucible for test, under the condition of 50 mL/min N$_2$, the sample was heated at a heating rate of 10° C./min from 30° C. (room temperature) to 300° C. (or 350° C.).

Thermal Gravimetric Analyzer (TGA) Method of the Present Invention

Instrument model: TA Q5000IR TGA Instrument

Test method: A sample (2-5 mg) was placed in a TGA platinum crucible for test, under the condition of 25 mL/min N$_2$, the sample was heated at a heating rate of 10° C./min from room temperature to 300° C. or a weight loss of 20%.

X-Ray Powder Diffractor (XRPD)

Test conditions: About 10-20 mg sample was used for XRPD detection.

X-ray tube: Cu, K-Alpha, (u, K-Alp Å)
X-ray tube voltage: 40 kV, X-ray tube current: 40 mA
Divergence slit: 0.60 mm
Detector slit: 10.50 mm
Anti-scattering slit: 7.10 mm
Scan range: 4-40 deg
Step length: 0.02 deg
Rate: 0.12 S
Rotation speed of sample tray: 15 rpm High Performance Liquid Chromatograph (HPLC)

The analytical method is as follows:

TABLE 8-1

Method for Measuring Content by HPLC Analysis*

| Instrument | Agilent 1200 High Performance Liquid Chromatograph (PDS-PF-HPLC-02 or PDS-PF-HPLC-01) | | |
|---|---|---|---|
| Column | Ascentis Express C18 (4.6 × 150 mm, 2.7 μm) (PDS-HPLC- | | |
| Mobile phase A | 0.1% phosphoric acid aqueous solution | | |
| Mobile phase B | 100% acetonitrile | | |
| Flow rate | 1 mL/min | | |
| Injection volume | 10 μL | | |
| Detection wavelength | 280 nm | | |
| Column | 40° C. | | |
| Diluent | N,N-dimethylformamide: acetonitrile 50/50 (v/v) or acetonitrile: water 1/1 (v/v) | | |
| Gradient elution procedure | Time (min) | Mobile phase A (%) | Mobile phase B (%) |
| | 0.00 | 90 | 10 |
| | 13.00 | 5 | 95 |
| | 15.00 | 5 | 95 |
| | 15.01 | 90 | 10 |
| | 18.00 | 90 | 10 |

*The method was used for detecting the crystal forms B and E in the specific embodiments.

TABLE 8-2

Method for Measuring Content by HPLC Analysis **

| Instrument | Agilent 1200 High Performance Liquid Chromatograph | | |
|---|---|---|---|
| Column | Agilent Eclipse C18 (4.6 × 150 mm, 3.5 μm) | | |
| Mobile phase A | 0.04% trifluoroacetic acid solution | | |
| Mobile phase B | 100% acetonitrile | | |
| Flow rate | 1 mL/min | | |
| Injection volume | 10 μL | | |
| Detection wavelength | 230 nm | | |
| Column temperature | 40° C. | | |
| Diluent | acetonitrile: water 50/50 (v/v) | | |
| Gradient elution procedure | Time | Mobile phase A | Mobile phase B |
| | 0.00 | 75 | 25 |
| | 50.00 | 30 | 70 |
| | 55.00 | 15 | 85 |
| | 55.01 | 75 | 25 |
| | 60 | 75 | 25 |

** The method was used for detecting the crystal forms A, C, D, and F in the specific embodiments.

Technical Effects

The crystal forms of the compounds represented by formula (I), (II) or (III) as described in the present disclosure have good stability and are easy to be made into medicaments; the core structure of the compound of the present disclosure having acrylamide and fluoroolefin bond can result in a series of highly FGFR4-selective compounds, which exhibits excellent inhibitory activity on FGFR4 kinase, but have no activity on the subtype of FGFR1 kinase, and the selectivity is at least 10 times or even more than 100 times.

DETAILED DESCRIPTION OF THE EMBODIMENTS

Figure 1:
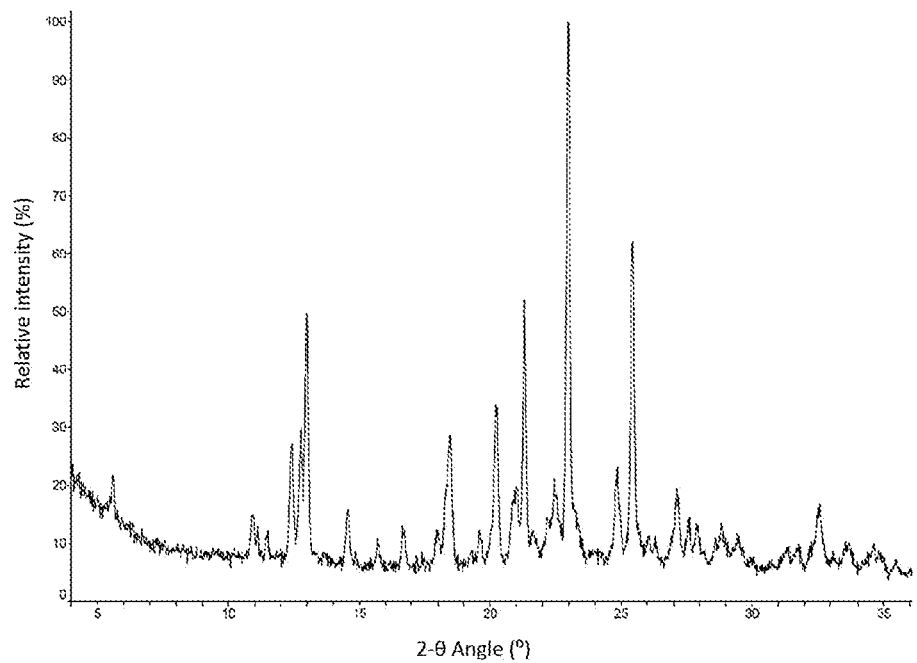
FIG. 1: the XRPD pattern measured by Cu-Kα radiation of the crystal form A of the compound represented by formula (I).

In order to better understand the content of the present disclosure, the following embodiments further illustrate the present disclosure, but the present disclosure is not limited thereto.

Embodiment 1: Synthesis of the Compound Represented by Formula (I)
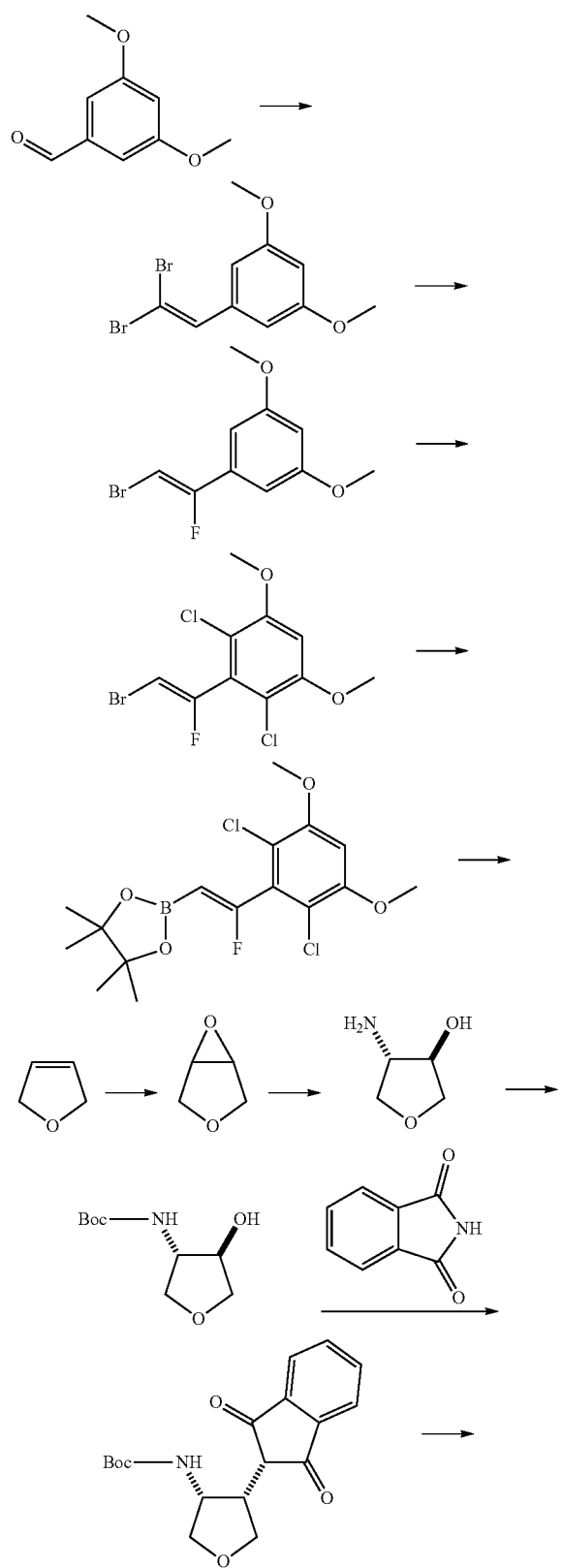
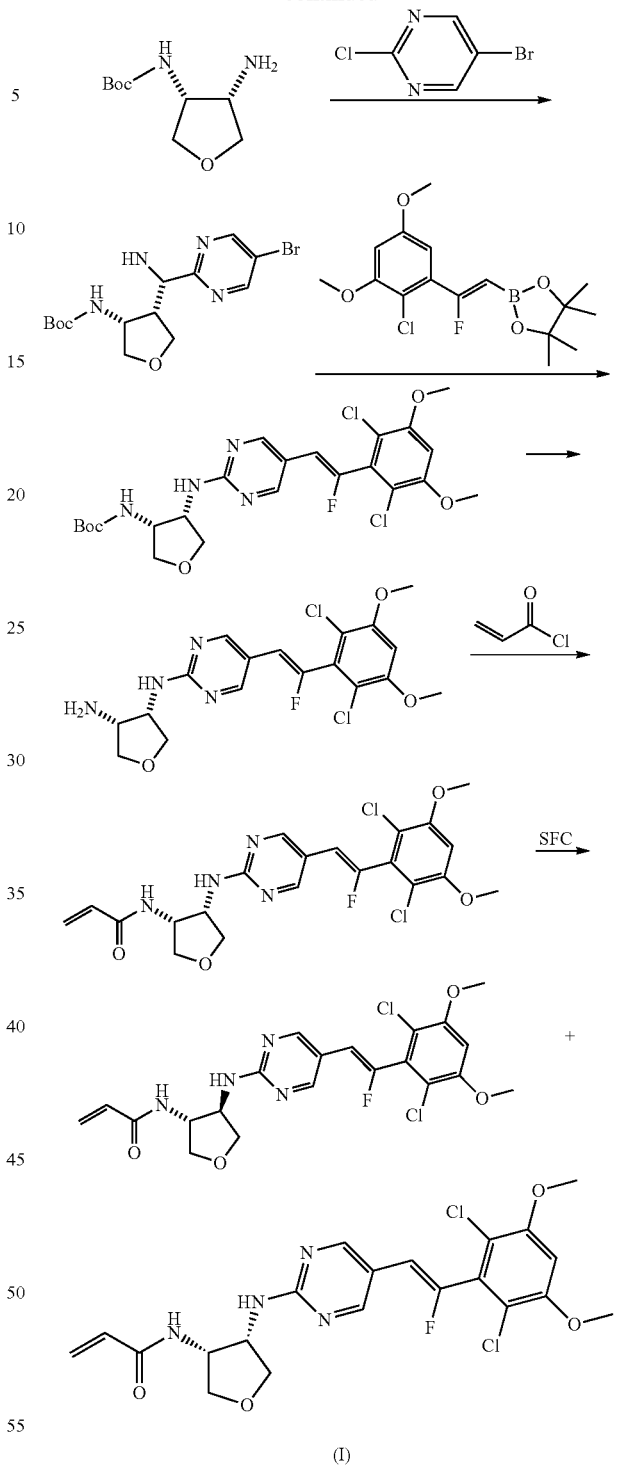
Embodiment 1A 2,5-dihydrofuran (80.00 g, 1.14 mol, 86.02 mL) was dissolved into 1000 mL DCM, then m-CPBA (277.74 g, 1.37 mol) was added in batches, and the reaction solution was reacted at room temperature for 14 hours. The reaction was monitored by TLC. After the completion of the reaction, the reaction solution was filtered to remove the solid, and the filtrate was washed with saturated sodium sulfite solution until starch-KI test paper does not turn blue, and then washed with saturated sodium bicarbonate solution until the pH of the solution was 7-8. The organic phase was dried over anhydrous sodium sulfate, filtered and subjected to rotary evaporation to remove the solvent to give 48.50 g yellow product of Embodiment 1A without further purification, the yield was 49.4%.

$^1$H NMR (400 MHz, CHLOROFORM-d) δ 3.99 (d, J=10.29 Hz, 2H), 3.77 (s, 2H), 3.63 (d, J=10.54 Hz, 2H).

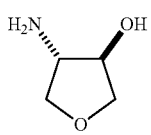

Embodiment 1B

Embodiment 1A (24.00 g, 278.78 mmol) and ammonium hydroxide (218.40 g, 1.74 mol, 240.00 mL) were added to a reaction flask, and the reaction solution was reacted at 100° C. for 14 hours. The reaction was monitored by TLC. After the completion of the reaction, the reaction solution was subjected to rotary evaporation to remove the solvent to give 23.70 g crude product of Embodiment 1B in brown oil form with a yield of 82.4%.

$^1$H NMR (400 MHz, CHLOROFORM-d) δ 4.00-4.16 (m, 3H), 3.63-3.81 (m, 1H), 3.48-3.59 (m, 1H), 3.34-3.45 (m, 1H).

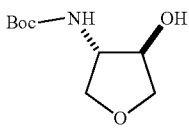

Embodiment 1C

Embodiment 1B (23.70 g, 229.83 mmol) was dissolved into 200 mL methanol, triethylamine (4.65 g, 45.97 mmol, 6.37 mL) was added, and Boc-anhydride (65.21 g, 298.78 mmol, 68.64 mL) was added dropwise, the reaction solution was reacted at room temperature for 3 hours. The reaction was monitored by TLC (preparative thin layer chromatograph). After the completion of the reaction, the reaction solution was subjected to rotary evaporation to remove the solvent, and then 100 mL methyl t-butyl ether was added. The reaction solution was stirred for 15 min and filtered. The resultant filter cake was the product, and no further purification was required. 38.78 g Embodiment 1C in pale yellow solid form was obtained with a yield of 83.0%.

$^1$H NMR (400 MHz, CHLOROFORM-d) δ 4.78 (br s, 1H), 4.24-4.31 (m, 1H), 3.98-4.13 (m, 2H), 3.94 (br s, 1H), 3.66-3.73 (m, 1H), 3.62 (dd, J=2.76, 9.29 Hz, 1H), 1.44 (s, 9H)

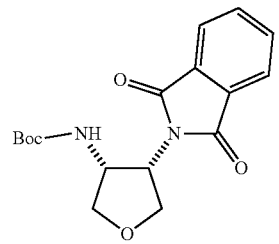

Embodiment 1D

Embodiment 1C (38.78 g, 190.82 mmol), phthalimide (33.69 g, 228.98 mmol) and triphenylphosphine (PPh$_3$) (60.06 g, 228.98 mmol) were dissolved into 500 mL THF, dimethyl azodicarboxylate (46.30 g, 228.98 mmol, 44.52 mL) was added, the obtained reaction solution was reacted at room temperature for 14 hours. The reaction was monitored by TLC. After the completion of the reaction, the reaction solution was subjected to rotary evaporation to remove the solvent, and purified by silica gel column (PE/EA=3/1, Rf=0.37) to give 85.50 g white solid product of Embodiment 1D.

$^1$H NMR (400 MHz, CHLOROFORM-d) δ 7.85-7.88 (m, 2H), 7.74-7.76 (m, 2H), 4.88 (br d, J=9.54 Hz, 1H), 4.44-4.55 (m, 1H), 4.37 (br t, J=8.16 Hz, 1H), 4.12-4.21 (m, 2H), 3.78-3.90 (m, 1H), 1.10 (s, 9H)

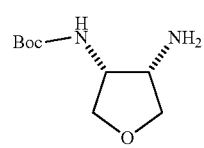

Embodiment 1E

Embodiment 1D (85.50 g, 257.26 mmol) was dissolved into 850 mL anhydrous ethanol, hydrazine hydrate (75.76 g, 2572.6 mmol, 73.55 mL) was added, and the obtained reaction solution was reacted at 80° C. for 1 hour. The reaction was monitored by TLC. After the completion of the reaction, the reaction solution was filtered to remove the generated white solid, and subjected to rotary evaporation to remove the solvent, followed by addition of 200 mL DCM. The reaction solution was filtered to remove the undissolved solid, and subjected to rotary evaporation to remove solvent to give 49.6 g crude product of embodiment 1E in light yellow solid form without further purification.

$^1$H NMR (400 MHz, CHLOROFORM-d) δ 5.32 (br s, 1H), 4.06-4.17 (m, 1H), 3.94-4.05 (m, 2H), 3.52-3.62 (m, 2H), 3.47 (dd, J=5.02, 9.03 Hz, 1H), 1.36-1.50 (m, 9H).

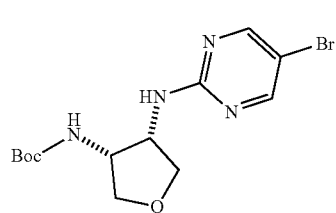

Embodiment 1F

Embodiment 1E (14.00 g, 69.22 mmol) and 2-chloro-5-bromopyrimidine (11.38 g, 58.84 mmol) were dissolved into 100 mL NMP, NaHCO$_3$ (17.45 g, 207.66 mmol) was added, and the obtained reaction was reacted at 110° C. for 14 hours. The reaction was monitored by TLC. After the completion of the reaction, 300 mL ethyl acetate was added, and then the reaction solution was washed with saturated brine (200 mL*3). The organic phase was dried over anhydrous sodium sulfate, filtered, subjected to rotary evaporation to remove the solvent, and purified by silica gel column (PE/EA=3/1, Rf=0.41) to give 15.66 g yellow solid of Embodiment 1F with a yield of 62.97%.

$^1$H NMR (400 MHz, CHLOROFORM-d) δ 8.30 (s, 2H), 5.71 (br s, 1H), 4.58-4.70 (m, 1H), 4.44 (br s, 1H), 4.03-4.11 (m, 2H), 3.63-3.73 (m, 2H), 2.04 (s, 4H), 1.38 (s, 9H).

Embodiment 16A

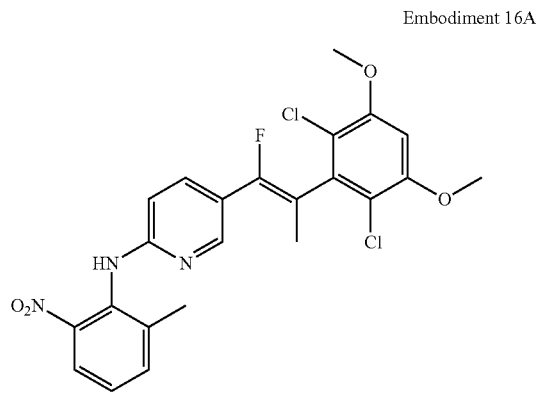

At 0° C., under nitrogen protection, tetrabromomethane (79.83 g, 240.72 mmol, 2.00 eq.) was added to a solution of triphenylphosphine (126.28 g, 481.43 mmol, 4.00 eq.) in dichloromethane (400.00 mL), and the obtained reaction solution was reacted at 0° C. for additional 5 min. 3,5-dimethoxybenzaldehyde (20.00 g, 120.36 mmol, 1.00 eq.) was added to the reaction solution, and the reaction solution was stirred at 0° C. for 4 hours. TLC detected that the starting materials were completely reacted, and a new point with a relatively high polarity was formed. Two batches of reaction solutions were combined, filtered, concentrated under vacuum, washed with 600 mL ethyl acetate, filtered, concentrated under vacuum, purified by column chromatography with a ratio of petroleum ether/ethyl acetate=20/1 to give a white solid of Embodiment 16A (39.92 g, yield: 84.20%).

$^1$H NMR (400 MHz, CHLOROFORM-d) Shift 7.42 (s, 1H), 6.69 (d, J=2.26 Hz, 2H), 6.46 (t, J=2.26 Hz, 1H), 3.80 (s, 6H)

Embodiment 16B

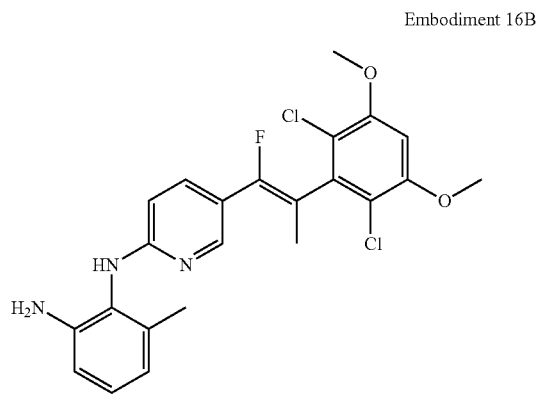 [SMILES: COc1cc(OC)c(Cl)c(/C(C)=C(\F)c2ccc(Nc3c(C)cccc3[N+](=O)[O-])nc2)c1Cl]

Tetrabutylammonium fluoride trihydrate (195.96 g, 621.10 mmol, 10.00 eq.) was added to a solution of Embodiment 16A (20.00 g, 62.11 mmol, 1.00 eq.) in toluene (600 mL), and the reaction solution was reacted at 110° C. for 16 hours. TLC showed that the starting materials were completely reacted. The reaction solution was diluted with 1200 mL water, and extracted with 900 mL ethyl acetate. The organic phase was dried over anhydrous sodium sulfate, filtered, concentrated under vacuum, and purified by column chromatography with a ratio of petroleum ether/ethyl acetate=20/1 to give a yellow liquid of Embodiment 16B (12.84 g, yield: 79.18%).

$^1$H NMR (400 MHz, CHLOROFORM-d) Shift 6.65 (d, J=2.26 Hz, 1H), 6.62 (d, J=2.26 Hz, 2H), 6.07-6.16 (m, 1H), 3.80 (s, 6H)

Embodiment 16C

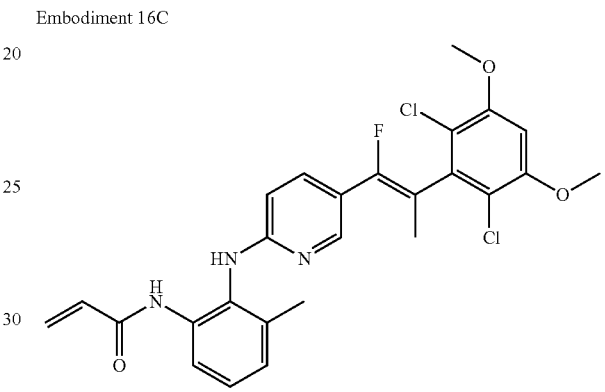

A solution of sulfonyl chloride (32.05 g, 237.48 mmol, 23.74 mL, 2.50 eq.) in tetrahydrofuran (15 mL) was added dropwise to a solution of Embodiment 16B (24.80 g, 94.99 mmol, 1.00 eq.) in tetrahydrofuran (500.00 mL) at −5° C., the reaction solution was reacted at −5° C. to 5° C. for 3 hours. An additional solution of sulfonyl chloride (1 mL) in tetrahydrofuran (10 mL) was added, and the reaction solution was reacted for another 1 hour at −5° C. to 5° C. TLC detected that the reaction was complete, and the reaction solution was quenched with a saturated aqueous solution of sodium bicarbonate (150 mL), and extracted with ethyl acetate (70 mL for each time) for three times. The organic phase was dried over anhydrous sodium sulfate, filtered, dried and concentrated, purified by column chromatography with a ratio of petroleum ether/ethyl acetate=9/1 to give a yellow solid of Embodiment 16C (27.75 g, yield: 88.53%).

$^1$H NMR (400 MHz, CHLOROFORM-d) Shift 6.57 (s, 1H), 5.78-5.87 (m, 1H), 3.94 (s, 6H)

Embodiment 16D

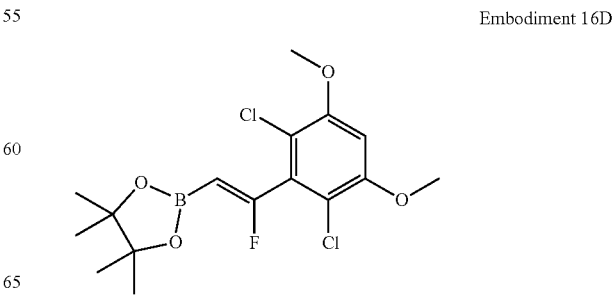

Tri(dibenzylideneacetone)dipalladium (5.55 g, 6.06 mmol, 0.10 eq.), tricyclohexylphosphine (6.80 g, 24.24 mmol, 0.40 eq.), and potassium acetate (23.79 g, 242.44 mmol, 4.00 eq.) were added to a solution of Embodiment 16C (20.00 g, 60.61 mmol, 1.00 eq.) and bis(pinacolato) diboron (30.78 g, 121.22 mmol, 2.00 eq.) in dioxane (300 mL), and the reaction solution was reacted at 90° C. under nitrogen protection for 16 hours. TLC detected that the reaction was complete, the reaction solution was filtered, concentrated under vacuum, and purified by column chromatography with a ratio of petroleum ether/ethyl acetate=4/1 to give a yellow solid of Embodiment 16D (16.82 g, yield: 73.60%).

¹H NMR (400 MHz, CHLOROFORM-d) Shift 6.59 (s, 1H), 4.82-4.97 (m, 1H), 3.92 (s, 6H), 1.25-1.28 (m, 12H), 1.17-1.19 (m, 1H)

Embodiment 1G

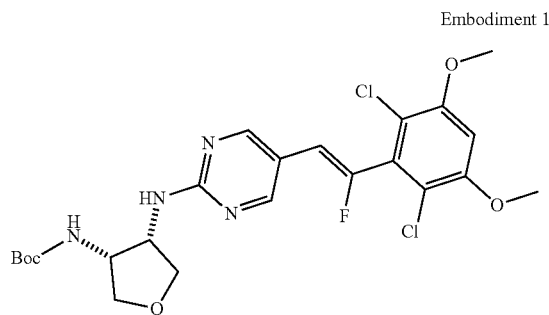

Embodiment 1F (15.62 g, 43.47 mmol) and Embodiment 16D (14.90 g, 39.52 mmol) were dissolved into 150 mL 1,4-dioxane and 75 mL water, Pd(dppf)Cl₂ (2.89 g, 3.95 mmol, 0.10 eq) and K₃PO₄ (16.78 g, 79.04 mmol, 2.00 eq) were added, and the obtained reaction solution was reacted at 95° C. under nitrogen protection for 14 hours. The reaction was monitored by TLC. After the completion of the reaction, 300 mL ethyl acetate was added, and then the reaction solution was washed with saturated brine (200 mL*3). The organic phase was dried over anhydrous sodium sulfate, filtered and subjected to rotary evaporation to remove the solvent, and purified by silica gel column (PE/EA=1/1, Rf=0.43) to give 4.6 g of a yellow solid of Embodiment 1G, the yield was 21.99%.

¹H NMR (400 MHz, CHLOROFORM-d) δ 8.57 (s, 2H), 6.64 (s, 1H), 5.79 (br d, J=6.53 Hz, 1H), 5.58-5.72 (m, 1H), 5.09 (br s, 1H), 4.70-4.80 (m, 1H), 4.47 (br s, 1H), 4.12-4.23 (m, 2H), 3.72 (br d, J=6.78 Hz, 2H), 1.39 (s, 9H)

Embodiment 1H

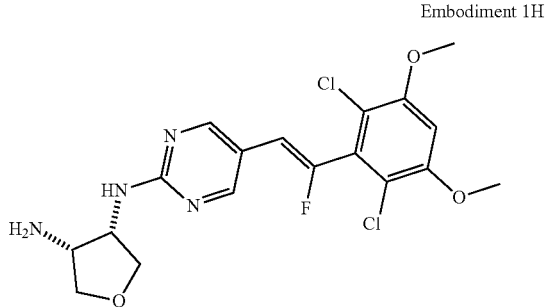

Embodiment 1G (4.60 g, 8.69 mmol) was dissolved into 30 mL DCM, trifluoroacetic acid (15.40 g, 135.04 mmol, 10.00 mL) was added dropwise, and the obtained reaction solution was reacted at room temperature for 30 min. The reaction was monitored by LC-MS. After the completion of the reaction, the solvent was removed by rotary evaporation, and 7.20 g tan solid crude product of Embodiment 1H was obtained without further purification.

LCMS (ESI): 429 (M+1)⁺

Embodiment 1I

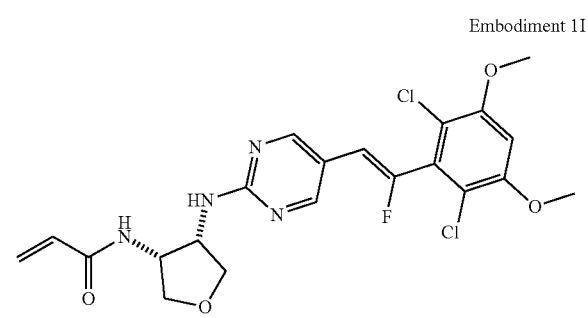

Embodiment 1H (7.20 g, 13.25 mmol) was dissolved into 40 mL DCM, and DIEA (6.85 g, 53.00 mmol, 9.26 mL) was added, the reaction solution was cooled to 0° C., acryloyl chloride (599.63 mg, 6.63 mmol, 540.21 uL) was added, the reaction solution was heated to room temperature and reacted for 20 min. The reaction was monitored by LC-MS, after the completion of the reaction, the reaction was quenched by adding 30 mL water, and then the reaction solution was extracted with DCM (15 mL*3), the organic phases were combined, and washed with 40 mL saturated brine, dried over anhydrous sodium sulfate, filtered, subjected to rotary evaporation to dryness, and purified by silica gel column (initially, PE/EA=1/1, and then DCM/MeOH=10/1) to give 2.7 g Embodiment 1I.

Compound represented by Formula (I)

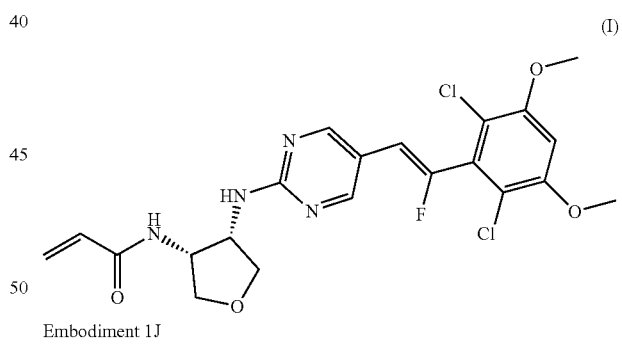

(I)

Embodiment 1J

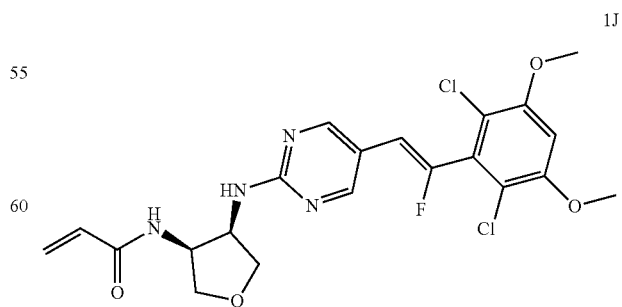

1J

Embodiment 1I (2.7 g, 5.59 mmol) was resolved by SFC (column: OD (250 mm*30 mm, 5 um); Mobile phase: [0.1%

NH$_3$H$_2$O EtOH]; B %: 40%-40%, 10 min) to give 830 mg Embodiment 1J (purity: 98.43%) with a retention time of 5.204, and 610 mg the compound represented by formula (I) (purity: 99.22%) with a retention time of 7.294.

Embodiment 1J: $^1$H NMR (400 MHz, CHLOROFORM-d) δ 8.57 (s, 2H), 6.65 (s, 1H), 6.38 (br d, J=6.53 Hz, 1H), 6.25 (dd, J=1.13, 16.94 Hz, 1H), 5.98-6.11 (m, 1H), 5.59-5.78 (m, 3H), 4.70-4.85 (m, 2H), 4.20 (ddd, J=6.02, 9.47, 12.36 Hz, 2H), 3.92-3.98 (m, 6H), 3.70-3.83 (m, 2H).

The compound represented by formula (I): $^1$H NMR (400 MHz, CHLOROFORM-d) δ 8.58 (s, 2H), 6.65 (s, 1H), 6.35 (br d, J=6.27 Hz, 1H), 6.21-6.29 (m, 1H), 5.99-6.10 (m, 1H), 5.59-5.74 (m, 3H), 4.69-4.82 (m, 2H), 4.20 (ddd, J=6.02, 9.47, 13.11 Hz, 2H), 3.95 (s, 6H), 3.77 (ddd, J=4.52, 9.54, 16.56 Hz, 2H).

Embodiment 2: Preparation of the Crystal Form A of the Compound Represented by Formula (I)

Figure 2:
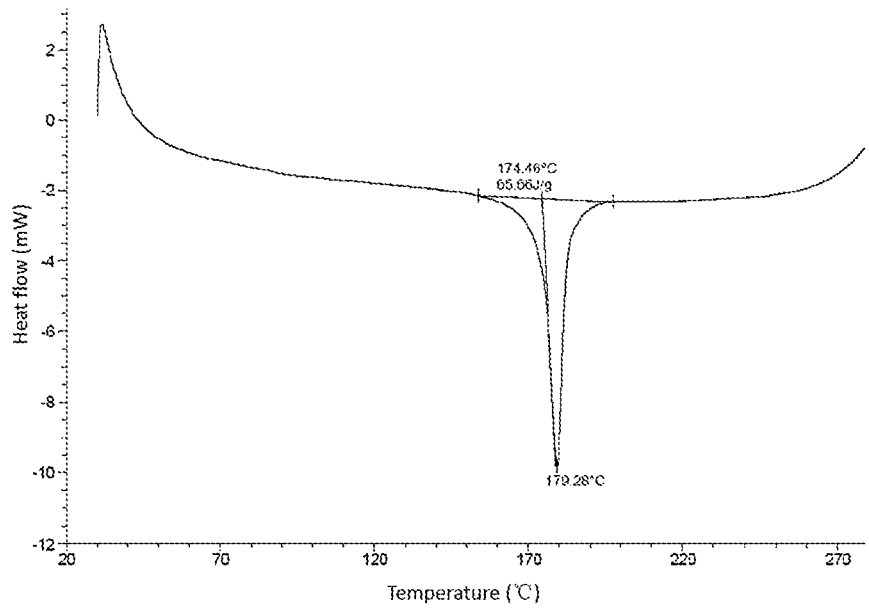
FIG. 2: the DSC pattern of the crystal form A of the compound represented by formula (I).
Figure 3:
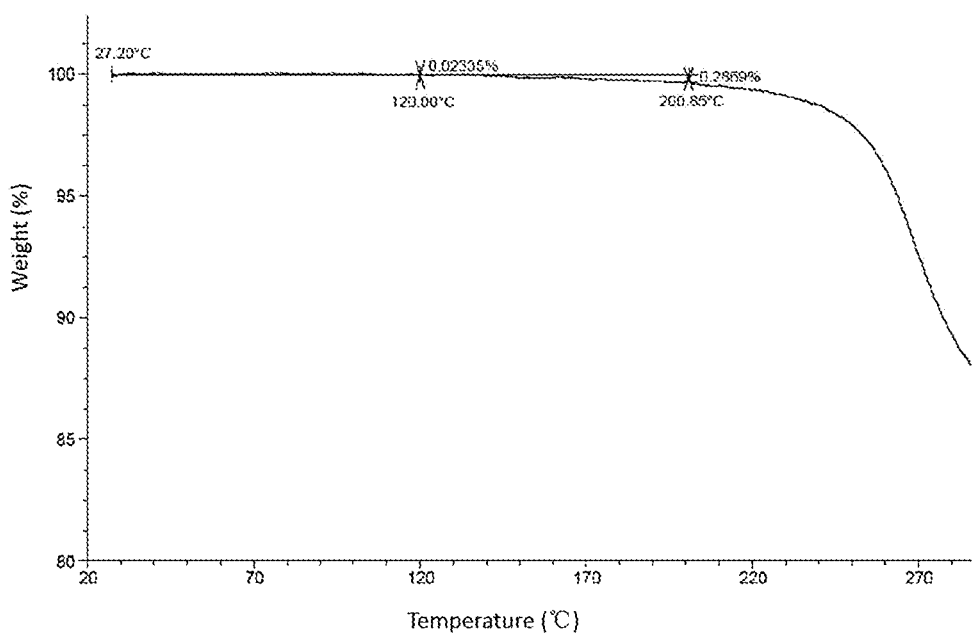
FIG. 3: the TGA pattern of the crystal form A of the compound represented by formula (I).

30 mg of the compound represented by formula (I) was weighed and added into a glass flask, 400 μL acetonitrile-water (1:1) was added to form a suspension. A sample of the suspension was placed on a magnetic stirrer (40° C.) for a dark stirring experiment. The sample of the suspension was centrifuged after stirring at 40° C. for 2 days, and then the residual sample was dried in a vacuum drying oven (30° C.) overnight to give a crystal form A of the compound represented by formula (I). The XRPD pattern of the crystal form A of the compound represented by formula (I) is shown in FIG. 1, the DSC pattern is shown in FIG. 2, and the TGA pattern is shown in FIG. 3.

In this Embodiment, the crystal form A was obtained after stirring in the acetonitrile-water system for 2 days, and thus it can be seen that the crystal form A has a substantially high stability in the acetonitrile-water solution.

Embodiment 3: Preparation of the Crystal Form A of the Compound Represented by Formula (I)

30 mg of the compound represented by formula (I) was weighed and added into a glass flask, and 400 μL ethyl acetate was added to form a suspension. A sample of the suspension was placed on a magnetic stirrer (40° C.) for dark stirring experiment. The sample of the suspension was centrifuged after stirring at 40° C. for 2 days, and then the residual sample was dried in a vacuum drying oven (30° C.) overnight. The crystal form was detected by XRPD to give a crystal form A of the compound represented by formula (I).

In this Embodiment, the crystal form A was obtained after stirring in the ethyl acetate system for 2 days, and thus it can be seen that the crystal form A has a substantially high stability in the ethyl acetate solution.

Embodiment 4: Preparation of the Crystal Form B of the Compound Represented by Formula (I)

Figure 4:
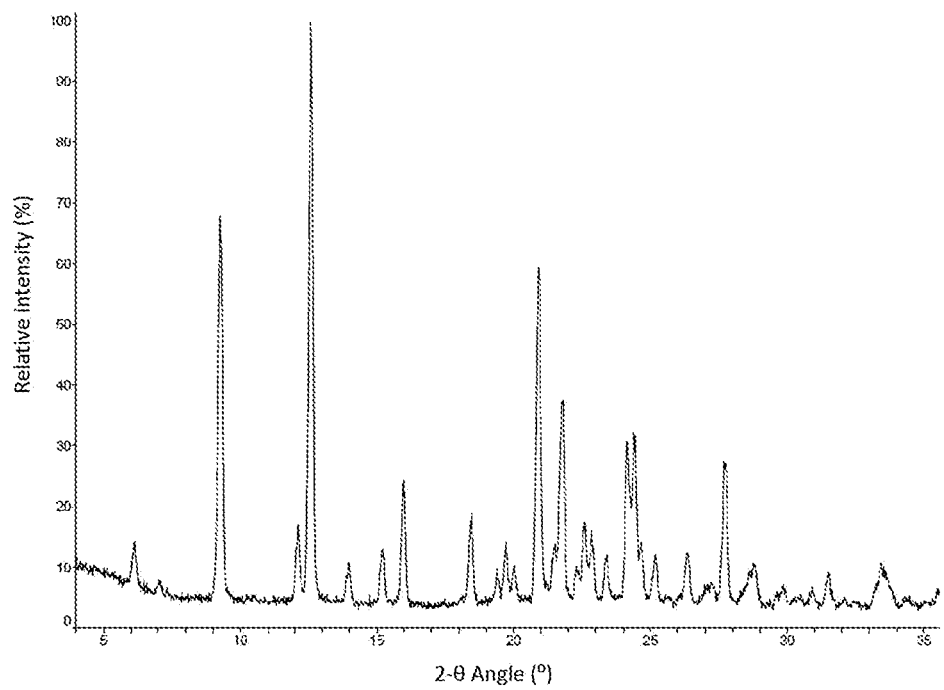
FIG. 4: the XRPD pattern measured by Cu-Kα radiation of the crystal form B of the compound represented by formula (I).
Figure 5:
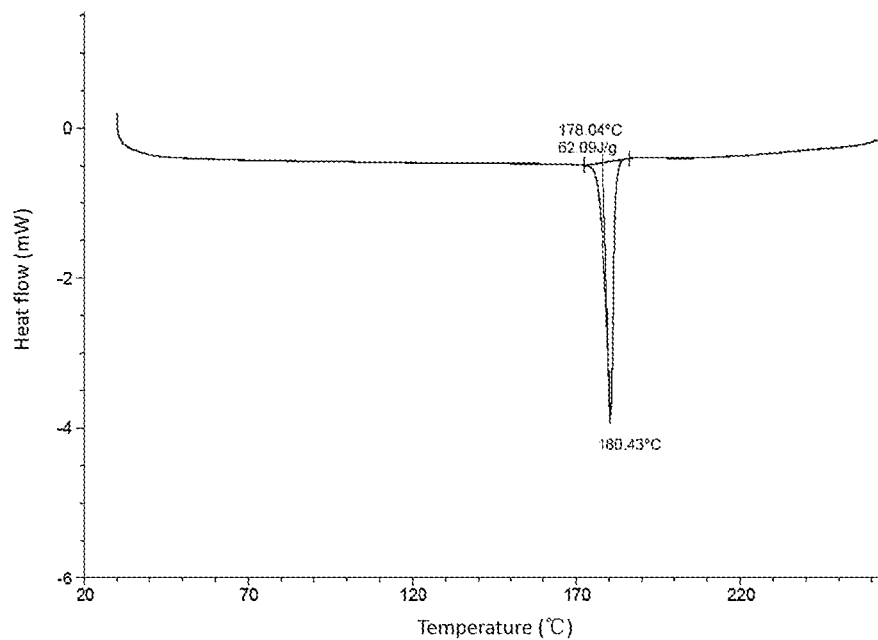
FIG. 5: the DSC pattern of the crystal form B of the compound represented by formula (I).
Figure 6:
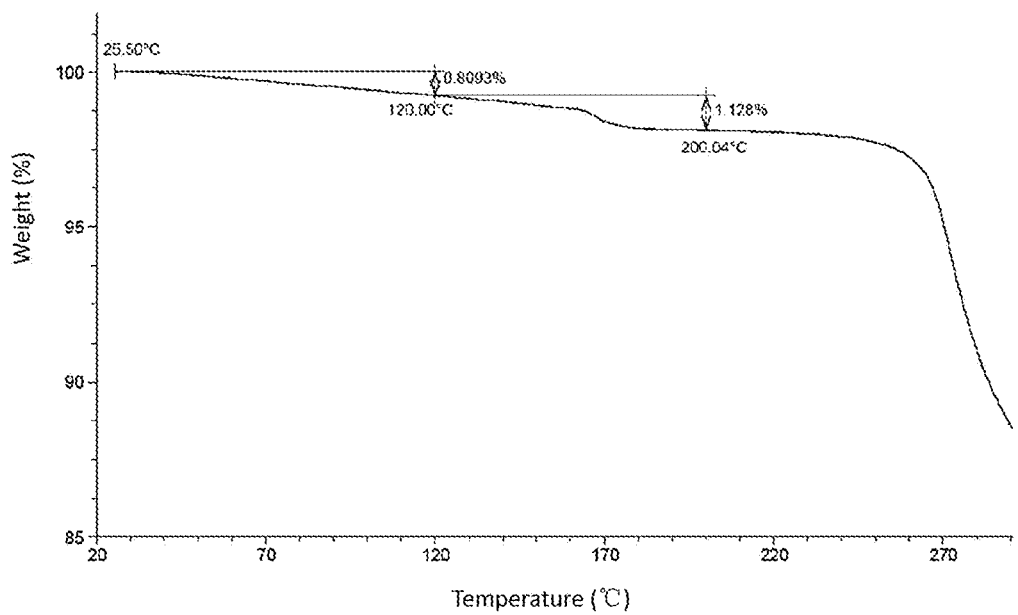
FIG. 6: the TGA pattern of the crystal form B of the compound represented by formula (I).

30 mg of the compound represented by formula (I) was weighed and added into a glass flask, and 400 μL methanol was added to form a suspension. A sample of the suspension was placed on a magnetic stirrer (40° C.) for dark stirring experiment. The sample of the suspension was centrifuged after stirring at 40° C. for 2 days, and then the residual sample was dried in a vacuum drying oven (30° C.) overnight to give a crystal form B of the compound represented by formula (I). The XRPD pattern of the crystal form B of the compound represented by formula (I) is shown in FIG. 4, the DSC pattern is shown in FIG. 5, and the TGA pattern is shown in FIG. 6.

In this Embodiment, the crystal form B was obtained after stirring in a methanol system for 2 days, and thus it can be seen that the crystal form B has a substantially high stability in the methanol solution.

Embodiment 5: Preparation of the Crystal Form B of the Compound Represented by Formula (I)

500 mg of the compound represented by formula (I) was weighed and added into a 10 mL glass flask, and 5 mL ethanol was added to form a suspension. A sample of the suspension was placed on a magnetic stirrer at 10-20° C. for stirring, and filtered after 12 hours. The residual solid of the sample was subjected to rotary evaporation to dryness, and subjected to XRPD detection for its crystal form to give a crystal form B of the compound represented by formula (I).

Embodiment 6: Preparation of the Crystal Form C of the Compound Represented by Formula (I)

Figure 7:
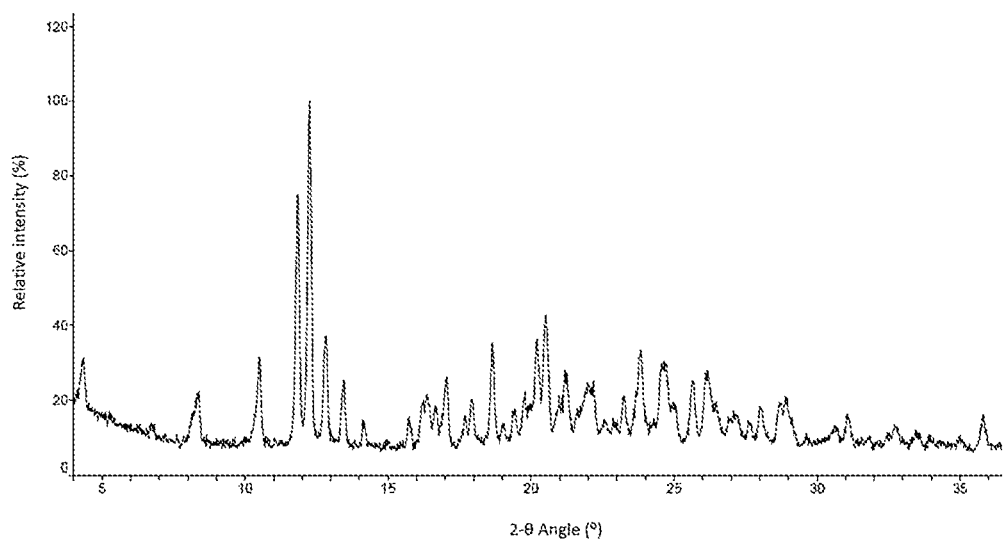
FIG. 7: the XRPD pattern measured by Cu-Kα radiation of the crystal form C of the compound represented by formula (I).
Figure 8:
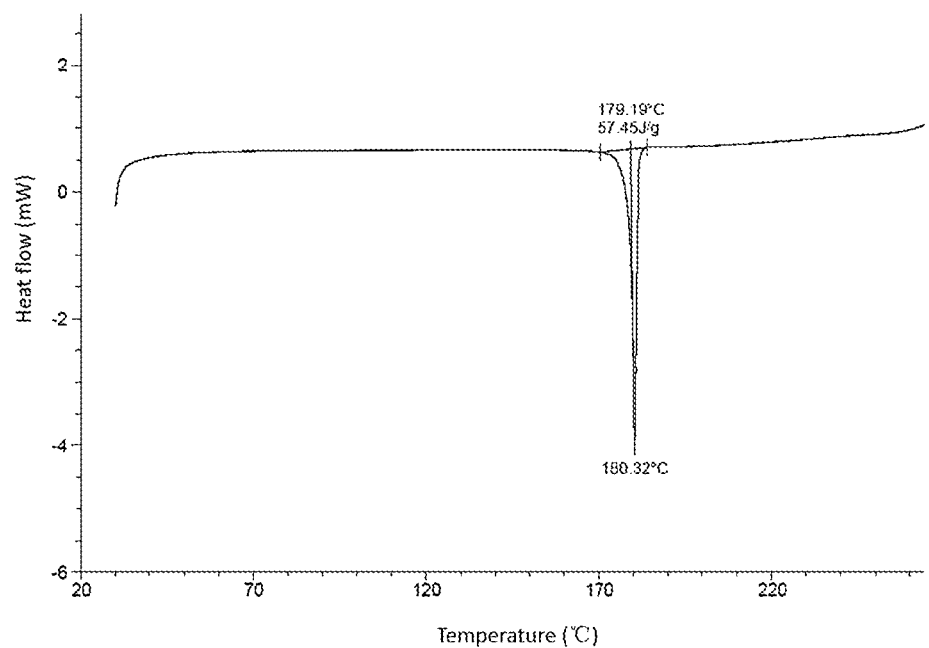
FIG. 8: the DSC pattern of the crystal form C of the compound represented by formula (I).
Figure 9:
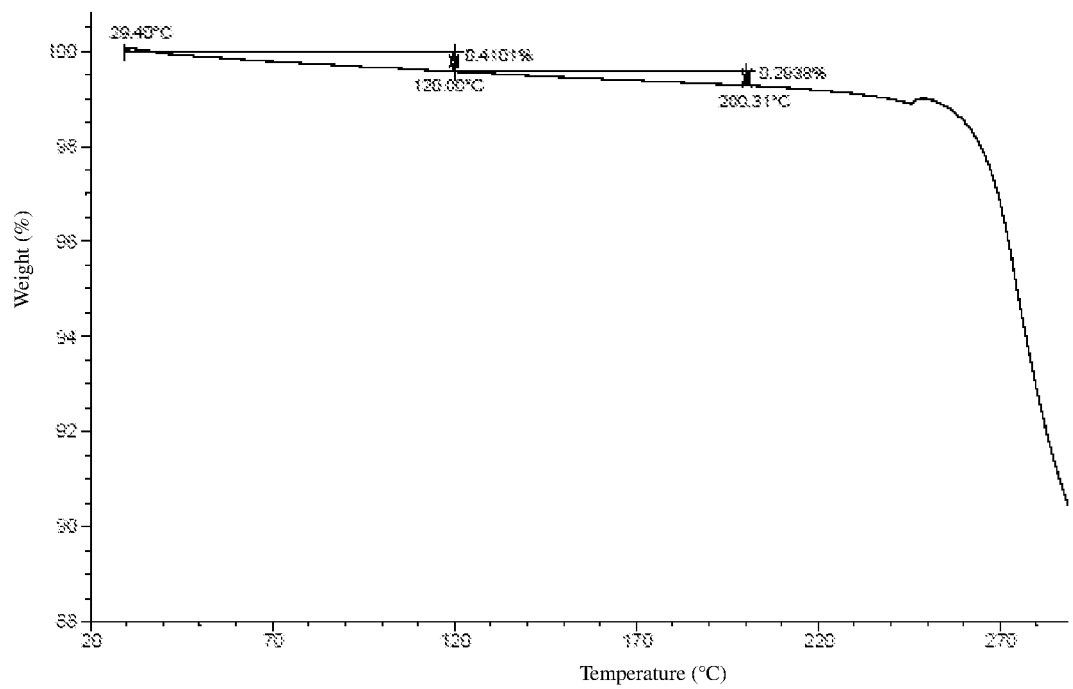
FIG. 9: the TGA pattern of the crystal form C of the compound represented by formula (I).

50 mg of the compound represented by formula (I) was weighed and added into a 1.5 mL liquid vial, and 200 μL methanol was added thereto, the obtained mixture was homogeneously mixed under ultrasound. The dissolved sample was quickly centrifuged, and the supernatant was placed in a centrifuge tube, the mouth of the tube was packed with a pierced aluminum foil, and then the tube was placed in a fume cupboard for volatilization; the sample of the suspension was placed on a magnetic stirring heater (40° C.) for stirring (in dark), and quickly centrifuged after 2 days. The resultant solid was collected and dried at 30° C. in a vacuum drying oven overnight to give the crystal form C of the compound represented by formula (I). The XRPD pattern of the crystal form C of the compound represented by formula (I) is shown in FIG. 7, the DSC pattern is shown in FIG. 8, and the TGA pattern is shown in FIG. 9.

In this Embodiment, the crystal form C was obtained after stirring in a methanol system for 2 days, and thus it can be seen that crystal form C has a substantially high stability in the methanol solution.

Embodiment 7: Preparation of the Crystal Form C of the Compound Represented by Formula (I)

500 mg of the compound represented by formula (I) was weighed and added into a 10 mL glass flask, and 5 mL solution of methanol-water (V$_{methanol}$-V$_{water}$=3:1) was added to form a suspension. A sample of the suspension was placed on a magnetic stirrer at 10-20° C. for stirring, and filtered after 12 hours, the residual solid of the sample was subjected to rotary-evaporation to dryness, and detected by XRPD for its crystal form status to give a crystal form C of the compound represented by formula (I).

Embodiment 8: Preparation of the Crystal Form D of the Compound Represented by Formula (I)

Figure 10:
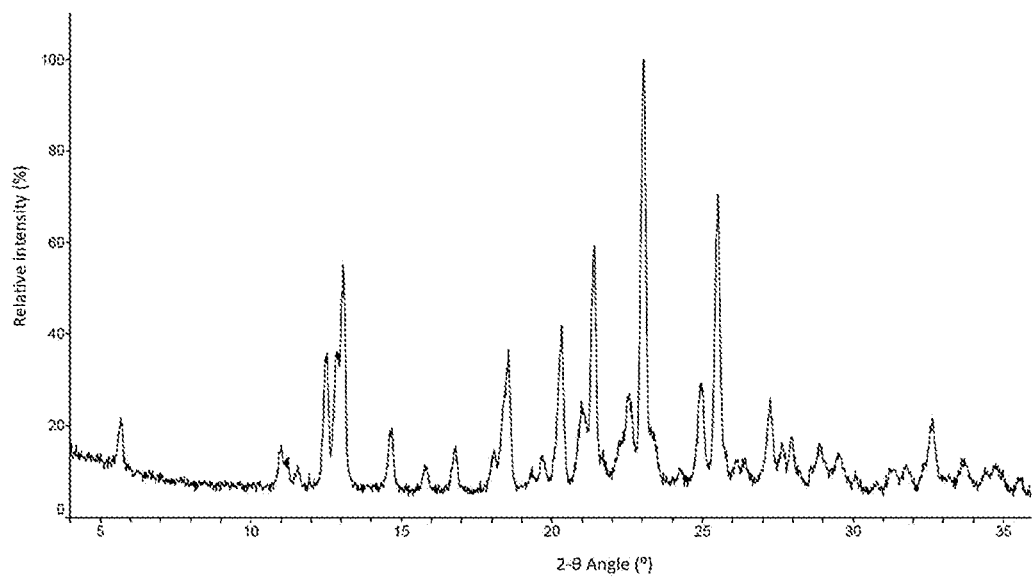
FIG. 10: the XRPD pattern measured by Cu-Kα radiation of the crystal form D of the compound represented by formula (I).
Figure 11:
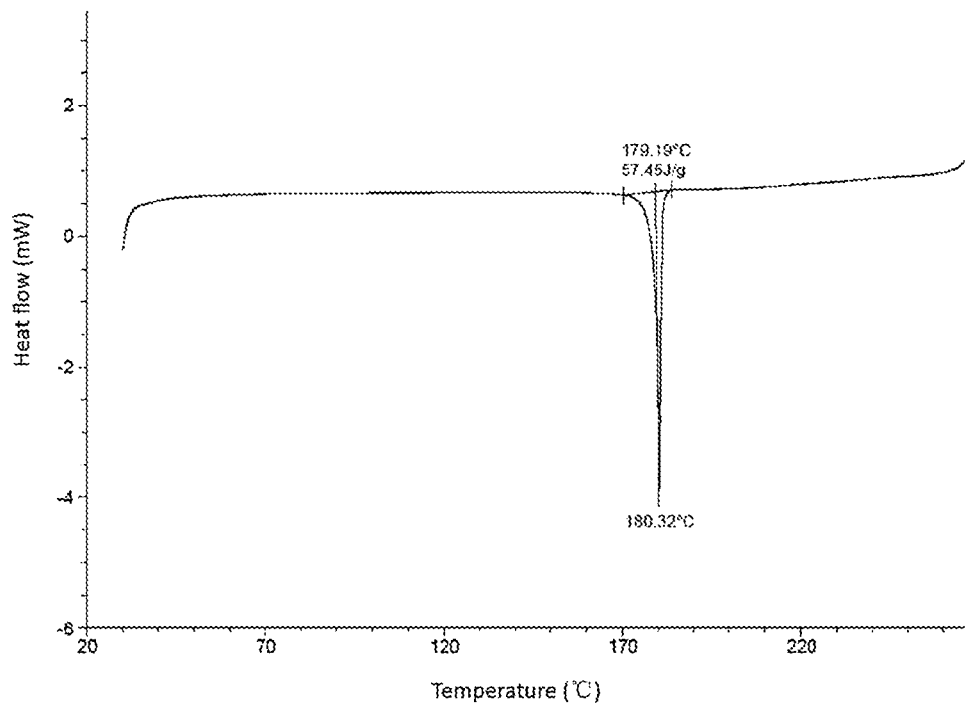
FIG. 11: the DSC pattern of the crystal form D of the compound represented by formula (I).
Figure 12:
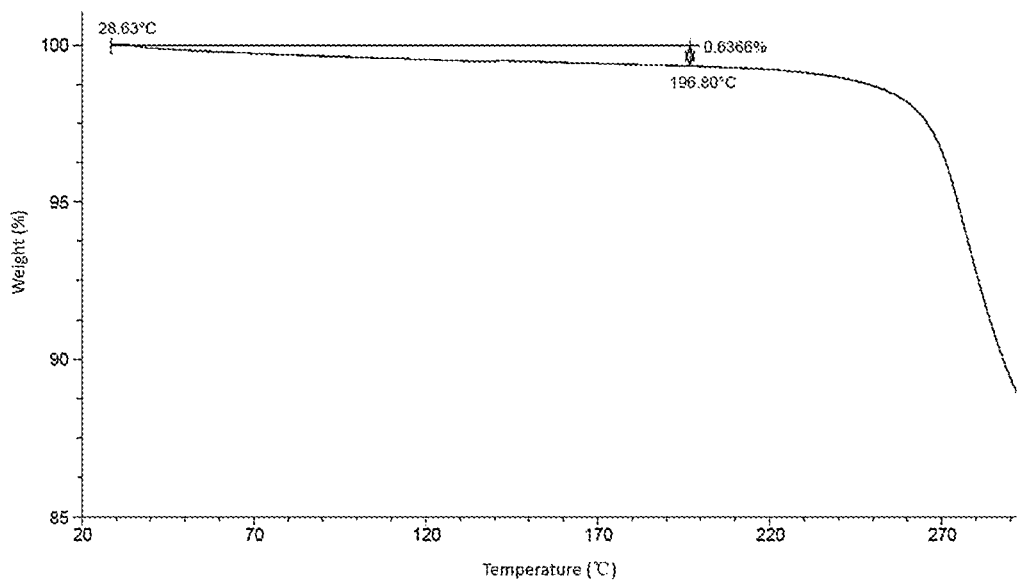
FIG. 12: the TGA pattern of the crystal form D of the compound represented by formula (I).

50 mg of the compound represented by formula (I) was weighed and added into a 1.5 mL liquid vial, and 200 μL ethanol was added thereto, and the obtained mixture was homogeneously mixed under ultrasound. The dissolved sample was quickly centrifuged, the supernatant was placed into a centrifuge tube, and the mouth of the tube was packed with a pierced aluminum foil, and placed in a fume cupboard for volatilization; the sample of the suspension was placed on a magnetic stirring heater (40° C.) for stirring (in dark), and quickly centrifuged after 2 days. The solid obtained as above was collected and dried at 30° C. in a vacuum drying oven overnight to give a crystal form D of the compound represented by formula (I). The XRPD pattern of the crystal form D of the compound represented by formula (I) is shown in FIG. 10, the DSC pattern is shown in FIG. 11, and the TGA pattern is shown in FIG. 12.

In this Embodiment, the crystal form D was obtained after stirring in an ethanol system for 2 days, and thus it can be seen that the crystal form D has a substantially high stability in the ethanol solution.

Embodiment 9: Preparation of the Crystal Form D of the Compound Represented by Formula (I)

500 mg of the compound represented by formula (I) was weighed and added into a 10 mL glass vial, and 2 mL ethanol was added thereto, the obtained mixture was homogeneously mixed under ultrasound. The dissolved sample was quickly centrifuged, and the supernatant was placed into a centrifuge tube, the mouth of the tube was packed with a pierced aluminum foil, and placed in a fume cupboard for about 12 hours of volatilization until the volume thereof was reduced to a half; the sample of the suspension was placed on a magnetic stirring heater (40° C.) for stirring (in dark), and quickly centrifuged after 2 days. The solid obtained as above was collected and dried at 30° C. in a vacuum drying oven overnight, and detected by XRPD for its crystal form status to give a crystal form D of the compound represented by formula (I).

Embodiment 10: Preparation of the Compound Represented by Formula (II)

5.8 g of the compound represented by formula (I) was weighed and added into a 250 mL single-neck flask, and 87.5 mL acetone solvent was added and stirred at 40° C. for dissolution; then, an appropriate amount of methanesulfonic acid (the molar ratio of the crystal form A of the compound represented by formula (I): the acid was 1:1.05) was added, the acid was diluted with the acetone solvent, and then slowly added into the solution of the active pharmaceutical ingredient, and the obtained mixture was observed for any phenomenon. A sample of the suspension was placed on a magnetic stirrer (40° C.) for stirring overnight. After stirring overnight, the methanesulfonate suspension was filtered, and subjected to rotary evaporation to dryness to give the compound represented by formula (II).

Embodiment 11: Preparation of the Crystal Form E of the Compound Represented by Formula (II)

Figure 13:
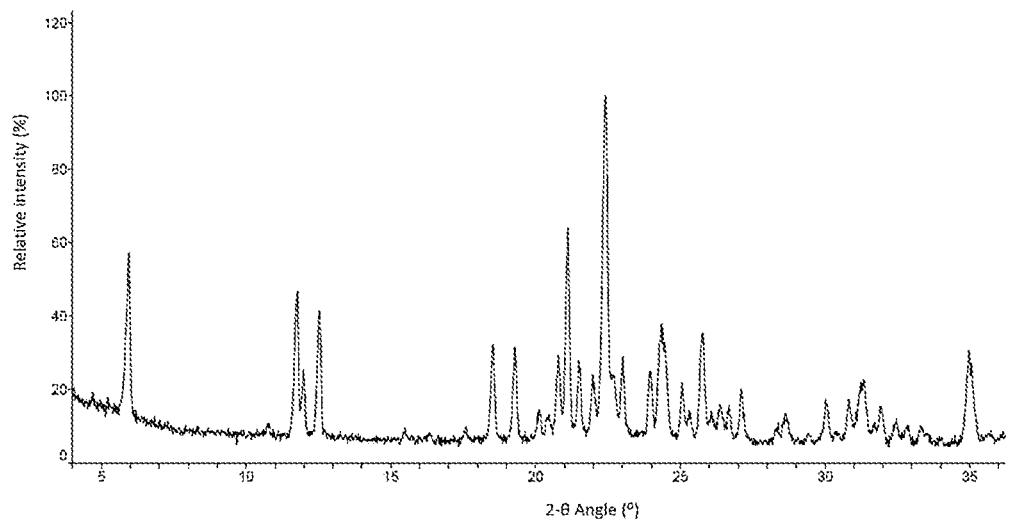
FIG. 13: the XRPD pattern measured by Cu-Kα radiation of the crystal form E of the compound represented by formula (II).
Figure 14:
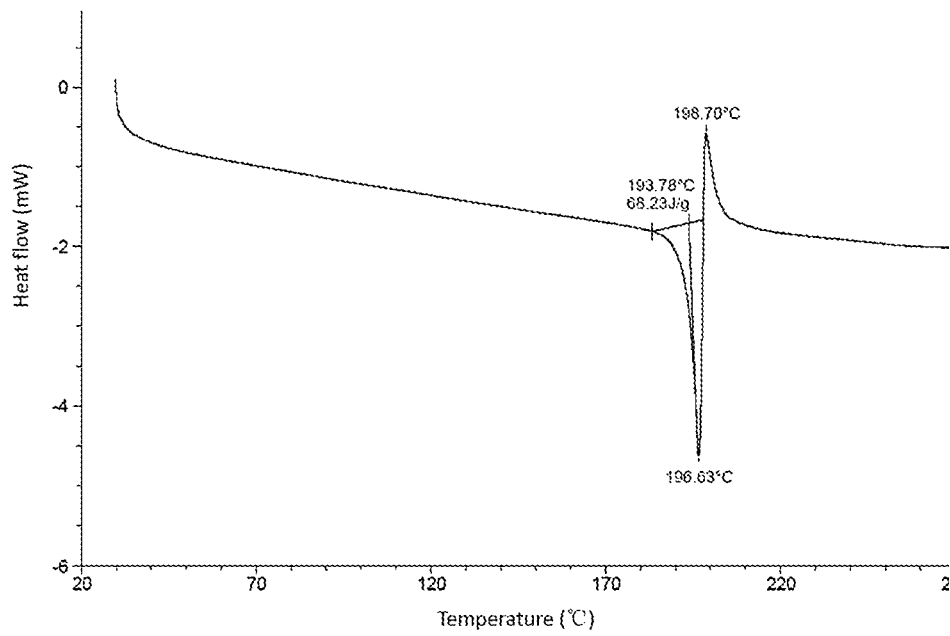
FIG. 14: the DSC pattern of the crystal form E of the compound represented by formula (II).
Figure 15:
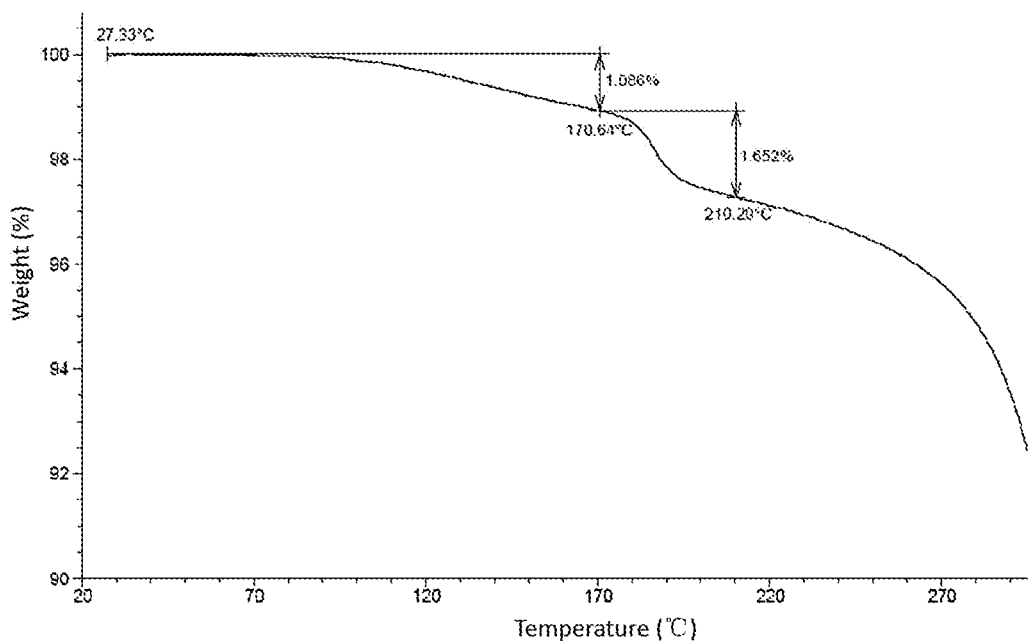
FIG. 15: the TGA pattern of the crystal form E of the compound represented by formula (II).

35 mg of the compound represented by formula (II) was weighed and added into a 1.5 mL liquid vial, and 400 μL methanol was added thereto, and the obtained mixture was homogeneously mixed under ultrasound. The dissolved sample was quickly centrifuged, and the supernatant was placed into a centrifuge tube, and the mouth of the tube was packed with a pierced aluminum foil, and placed in a fume cupboard for volatilization. The sample of the suspension was placed on a magnetic stirring heater (40° C.) for stirring (in dark) and quickly centrifuged after 2 days. The obtained solid was collected and dried at room temperature in a vacuum drying oven to give a crystal form E of the compound represented by formula (II). The XRPD pattern of the crystal form E of the compound represented by formula (II) is shown in FIG. 13, the DSC pattern is shown in FIG. 14, and the TGA pattern is shown in FIG. 15.

In this Embodiment, the crystal form E was obtained after stirring in a methanol system for 2 days, and thus it can be seen that the crystal form E has a substantially high stability in the methanol solution.

Embodiment 12: Preparation of the Crystal Form E of the Compound Represented by Formula (II)

350 mg of the compound represented by formula (II) was weighed and added into a 10 mL single-neck flask, 4 mL methanol was added thereto, the obtained mixture was homogeneously mixed under ultrasound. The dissolved sample was quickly centrifuged, and the supernatant was placed into a centrifuge tube, and the mouth of the tube was packed with a pierced aluminum foil, and placed in a fume cupboard for about 12 hours of volatilization until the volume thereof was reduced to a half; the sample of the suspension was placed on a magnetic stirring heater at 40° C. for stirring in dark and quickly centrifuged after 2 days. The obtained solid was collected and dried at room temperature in a vacuum drying oven, and detected by XRPD for its crystal form status to give a crystal form E of the compound represented by formula (II).

Embodiment 13: Preparation of the Crystal Form F of the Compound Represented by Formula (II)

Figure 16:
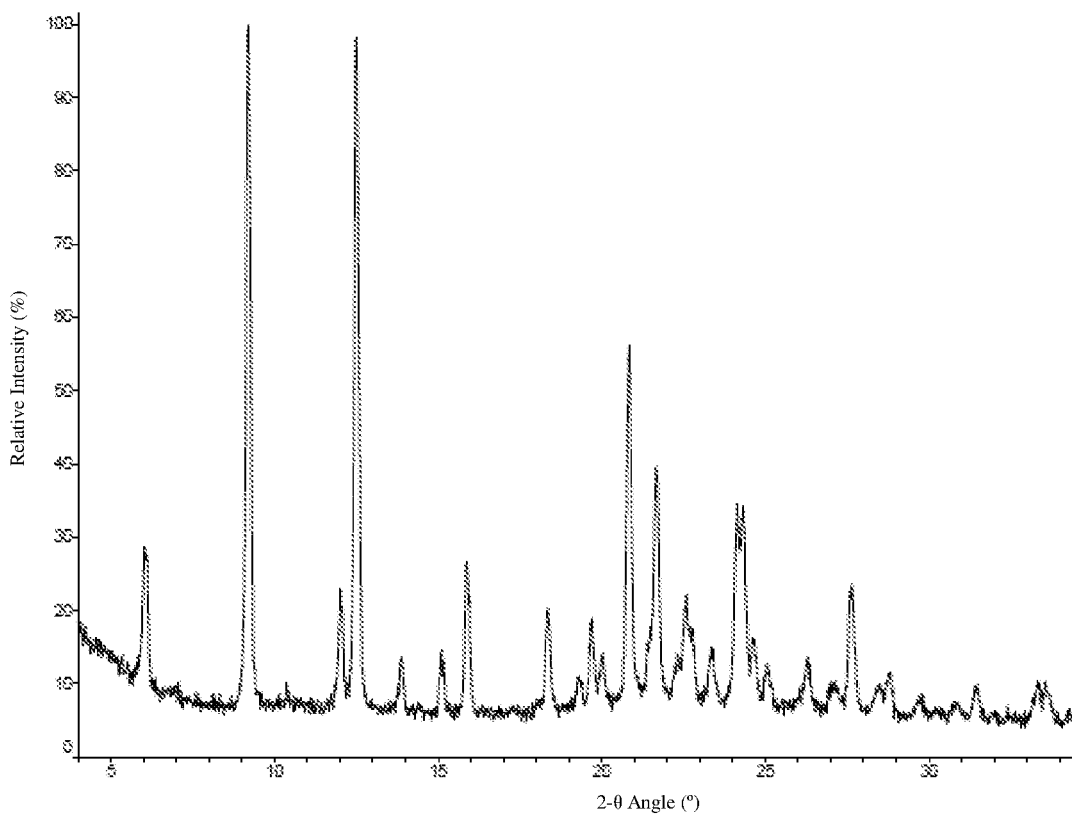
FIG. 16: the XRPD pattern measured by Cu-Kα radiation of the crystal form F of the compound represented by formula (II).
Figure 17:
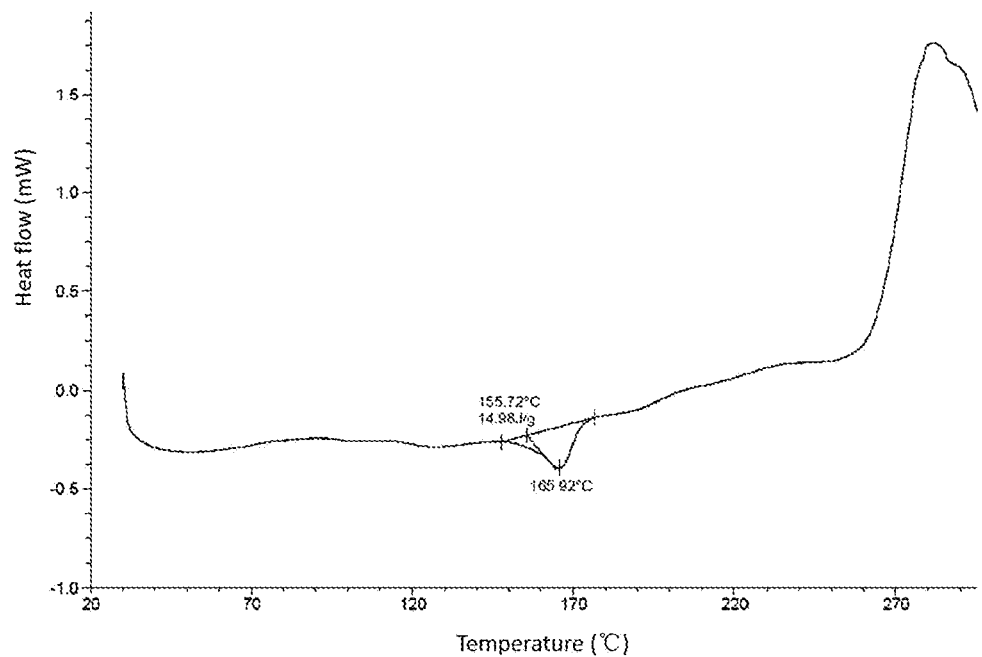
FIG. 17: the DSC pattern of the crystal form F of the compound represented by formula (II).
Figure 18:
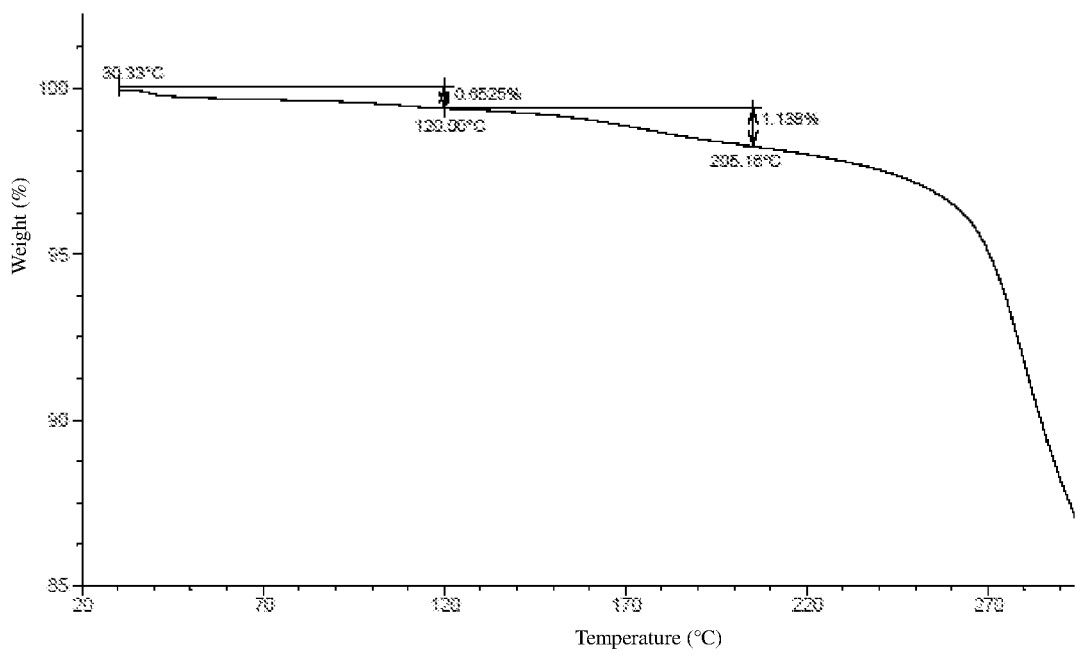
FIG. 18: the TGA pattern of the crystal form F of the compound represented by formula (II).

35 mg of the compound represented by formula (II) was weighed and added into a 1.5 mL liquid vial, 400 μL ethanol-water (1:1) was added thereto, and the obtained mixture was homogeneously mixed under ultrasound. The dissolved sample was quickly centrifuged, and the supernatant was placed into a centrifuge tube, and the mouth of the tube was packed with a pierced aluminum foil, and placed in a fume cupboard for volatilization; the sample of the suspension was placed on a magnetic stirring heater (40° C.) for stirring (in dark) and quickly centrifuged after 2 days. The obtained solid was collected and dried at room temperature in a vacuum drying oven to give a crystal form F the compound represented by formula (II). The XRPD pattern of the crystal form F of the compound represented by formula (II) is shown in FIG. 16, the DSC pattern is shown in FIG. 17, and the TGA pattern is shown in FIG. 18.

In this Embodiment, the crystal form F was obtained by stirring in an ethanol-water system for 2 days, and thus it can be seen that the crystal form F has a substantially high stability in the ethanol-water solution.

Embodiment 14: Preparation of the Crystal Form F of the Compound Represented by Formula (II)

350 mg of the compound represented by formula (II) was weighed and added into a 10 mL glass flask, 4 mL ethanol-water (1:1) was added thereto, the obtained mixture was homogeneously mixed under ultrasound. The dissolved sample was quickly centrifuged, and the supernatant was placed into a centrifuge tube, and the mouth of the tube was packed with a pierced aluminum foil, and placed in a fume cupboard for about 12 hours of volatilization until the volume thereof was reduced to a half. The sample of the suspension was placed on a magnetic stirring heater at 40° C. for stirring in dark and quickly centrifuged after 2 days. The obtained solid was collected and dried at room temperature in a vacuum drying oven, and detected by XRPD for its crystal form status to give a crystal form F of the compound represented by formula (II).

Embodiment 15: Preparation of the Crystal Form G of the Compound Represented by Formula (III)

Figure 19:
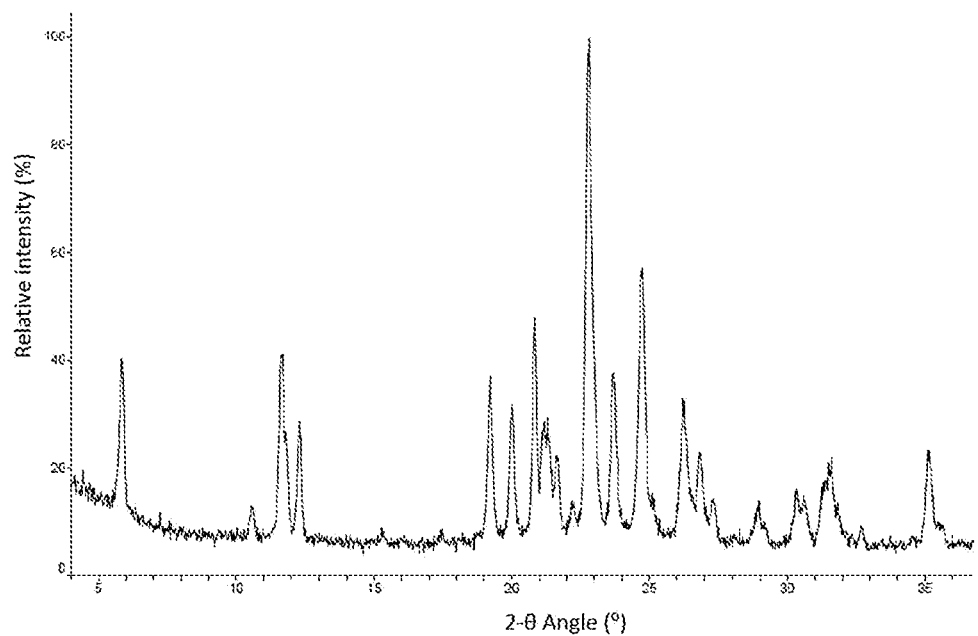
FIG. 19: the XRPD pattern measured by Cu-Kα radiation of the crystal form G of the compound represented by formula (III).
Figure 20:
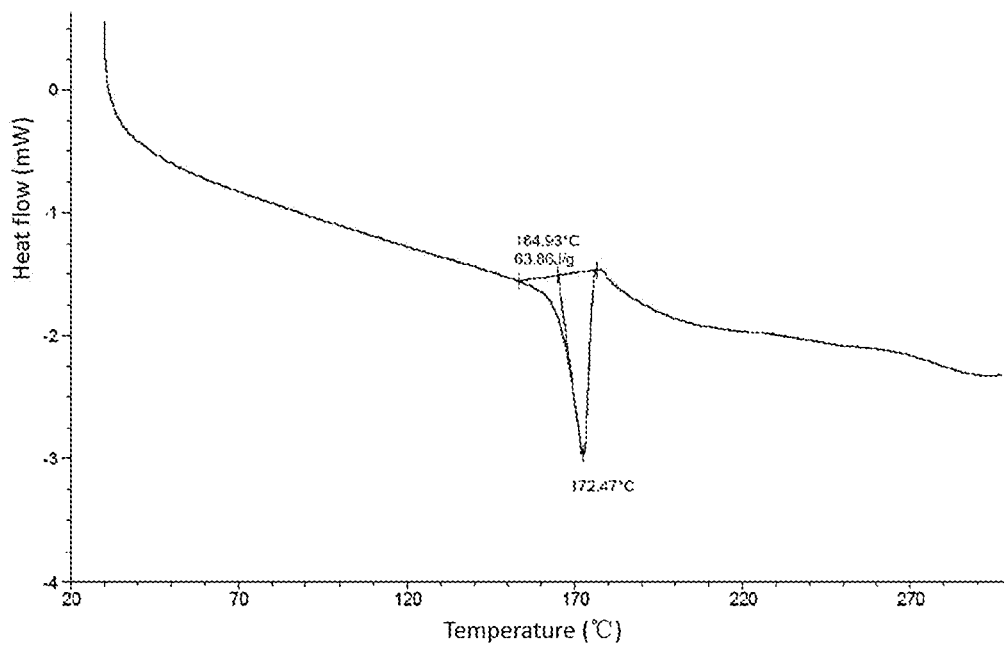
FIG. 20: the DSC pattern of the crystal form G of the compound represented by formula (III).
Figure 21:
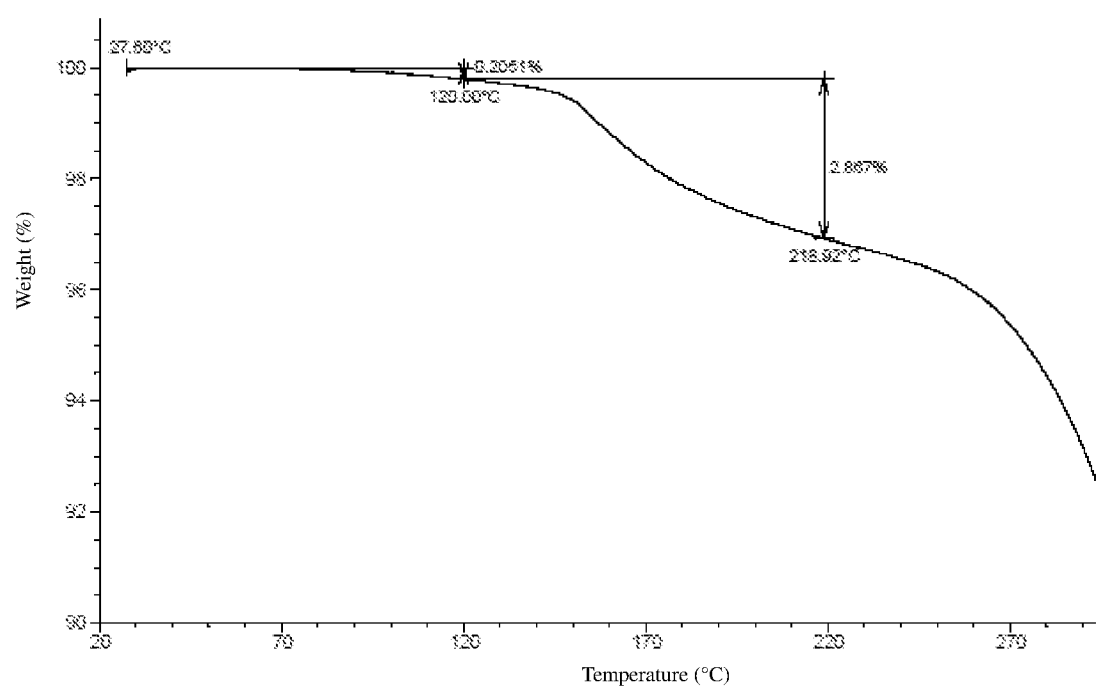
FIG. 21: the TGA pattern of the crystal form G of the compound represented by formula (III).

100 mg of the compound represented by formula (I) was weighed and added into a 8 mL glass vial, 1.5 mL acetone was added thereto, the obtained mixture was subjected to ultrasonic treatment for dissolution. Then, an appropriate amount of sulfuric acid was taken (the molar ratio of API:acid was 1:1.05), the acid was diluted with acetone or dissolved by ultrasound, and slowly added into a solution of the active pharmaceutical ingredient in acetone, the mixture was observed for any phenomenon. The solution or suspension sample was placed on a magnetic stirrer (40° C.) for stirring. After stirring overnight, the sample suspension was centrifuged, and dried at 30° C. in a vacuum drying oven overnight to give a crystal form G of the compound represented by formula (III). The XRPD pattern of the crystal form G of the compound represented by formula (III) is shown in FIG. 19, the DSC pattern is shown in FIG. 20, and the TGA pattern is shown in FIG. 21.

In this embodiment, the crystal form G was obtained by stirring in an acetone system for 2 days, and thus it can be seen that the crystal form G has a substantially high stability in the acetone solution.

Experimental Embodiment 1: Solid Stability Test of the Crystal Form A

A sample of the crystal form A was placed on the bottom of a glass sample bottle, and spread to a thin layer. The sample stored under high temperature, high humidity, and acceleration conditions was placed in a bottle of which the mouth was packed with a pierced aluminum foil to ensure the sample to be sufficiently exposed to ambient air; the sample stored under light radiation conditions was placed at room temperature in a standing bottle of which the mouth was open, the sample was exposed to a light resource, and sampled for detection after being radiated by sufficient energy. Samples were taken and analyzed at various time points, and the test results were compared with the initial test results of 0 day, the inspection items included appearance, content and impurities, and the test results are shown in Table 9.

TABLE 9

Solid Stability Test of the Crystal Form A

| Conditions | Time Points | Appearance | Content (%) | Total Impurities (%) |
|---|---|---|---|---|
| — | 0 day | Off-white solid | 99.11 | 1.12 |
| High temperature (60° C., open) | 5 days | Off-white solid | Not detected | Not detected |
| | 10 days | Off-white solid | 99.06 | 1.18 |
| High humidity (room temperature/ relative humidity of 92.5%, open) | 5 days | Off-white solid | Not detected | Not detected |
| | 10 days | Off-white solid | 98.85 | 1.22 |
| Light radiation (total illumination: 1.2 × 10$^6$ Lux · hr/) | 5 days | Off-white solid | Not detected | Not detected |
| | 10 days | Off-white solid | 99.13 | 1.10 |

TABLE 9-continued

Solid Stability Test of the Crystal Form A

| Conditions | Time Points | Appearance | Content (%) | Total Impurities (%) |
|---|---|---|---|---|
| Acceleration test (40° C./relative humidity of 75%, open) | 5 days | Off-white solid | Not detected | Not detected |
| | 10 days | Off-white solid | 98.98 | 1.18 |

Conclusion: The influence factors and acceleration tests showed that the crystal form A exhibits relatively good thermal stability, photostability and stability under acceleration conditions, but has slightly less stability under high humidity conditions.

Experimental Embodiment 2: Solid Stability Test of the Crystal Form B

A sample of the crystal form B (10 mg) was placed on the bottom of a glass sample bottle, and spread to a thin layer. The sample stored under high temperature, high humidity, and acceleration conditions were placed in a bottle of which the mouth was packed with a pierced aluminum foil to ensure the sample to be sufficiently exposed to ambient air; the sample stored under light radiation conditions was placed at room temperature in a standing bottle of which the mouth was open, the sample was exposed to a light resource, and sampled for detection after being radiated by sufficient energy, the control sample stored in dark (open, the whole sample bottle was sealed with aluminum foil to keep the content in dark) and the sample stored under light radiation conditions were placed together to exclude environmental influence on the samples. Samples were taken and analyzed at various time points, and the test results were compared with the initial test results of 0 day, the inspection items included appearance, crystal form, content and impurities, the test results are shown in Table 10.

TABLE 10

Solid Stability Test of the Crystal Form B

| Conditions | Time Points | Appearance | Crystal Form (XRPD) | Content (%) | Total Impurities (%) |
|---|---|---|---|---|---|
| — | 0 day | Off-white solid | Crystal form B | 99.21 | 0.41 |
| High temperature (60° C., open) | 5 days | Off-white solid | Crystal form B | Not detected | Not detected |
| | 10 days | Off-white solid | Crystal form B | 100.74 | 0.42 |
| High humidity (room temperature/ relative humidity of 92.5%, open) | 5 days | Off-white solid | Crystal form B | Not detected | Not detected |
| | 10 days | Off-white solid | Crystal form B | 101.03 | 0.42 |
| Light radiation (total illumination: 1.2 × 10$^6$ Lux · hr/near ultraviolet: 200 w · hr/m$^2$, open) | Light radiation | Off-white solid | Crystal form B | 92.90 | 2.21 |
| | In dark | Off-white solid | Crystal form B | 100.23 | 0.42 |

TABLE 10-continued

Solid Stability Test of the Crystal Form B

| Conditions | Time Points | Appearance | Crystal Form (XRPD) | Content (%) | Total Impurities (%) |
|---|---|---|---|---|---|
| Acceleration test (40° C./relative humidity of 75%, open) | 10 days | Off-white solid | Crystal form B | 101.21 | 0.43 |
| | 1 month | Off-white solid | Crystal form B | 99.49 | 0.43 |
| | 2 months | Off-white solid | Crystal form B | Not detected | Not detected |
| | 3 months | Off-white solid | Crystal form B | 96.23 | 0.31 |
| Acceleration test (60° C./relative humidity of 75%, open) | 10 days | Off-white solid | Crystal form B | 100.91 | 0.42 |
| | 1 month | Off-white solid | Crystal form B | 98.68 | 0.42 |
| | 2 months | Off-white solid | Crystal form B | Not detected | Not detected |
| | 3 months | Off-white solid | Crystal form B | 96.71 | 0.31 |

Conclusion: the influence factors and acceleration tests all showed that the crystal form B exhibits superior thermal stability and stability under acceleration conditions, and exhibits slight impurity generation under light radiation, and good stability in dark.

Experimental Embodiment 3: Solid Stability Test of the Crystal Form C

A sample of the crystal form C was taken and placed on the bottom of a glass sample bottle, and spread to a thin layer. The sample stored under high temperature, high humidity, and acceleration conditions was placed in a bottle of which the mouth was packed with a pierced aluminum foil to ensure the sample to be sufficiently exposed to ambient air; the sample stored under light radiation conditions was placed at room temperature in a standing bottle of which the mouth was open, the sample was exposed to a light resource, and sampled for detection after being radiated by sufficient energy. Samples were taken and analyzed at various time points, and the test results were compared with the initial test results of 0 day. The inspection items included appearance, crystal form, content and impurities, the test results are shown in Table 11.

TABLE 11

Solid Stability Test of the Crystal Form C

| Conditions | Time Points | Appearance | Crystal Form (XRPD) | Content (%) | Total Impurities (%) |
|---|---|---|---|---|---|
| — | 0 day | Off-white solid | Crystal form C | 98.96 | 1.25 |
| High temperature (60° C., open) | 5 days | Off-white solid | Not detected | Not detected | Not detected |
| | 10 days | Off-white solid | Crystal form C | 98.93 | 1.27 |
| High humidity (room temperature/ relative humidity of 92.5%, open) | 5 days | Off-white solid | Not detected | Not detected | Not detected |
| | 10 days | Off-white solid | Crystal form C | 98.22 | 2.08 |
| Light radiation (total illumination: 1.2 × 10^6 Lux · hr/) | 5 days | Off-white solid | Not detected | Not detected | Not detected |
| | 10 days | Off-white solid | Crystal form C | 98.35 | 1.86 |
| Acceleration test (40° C./relative humidity of 75%, open) | 5 days | Off-white solid | Not detected | Not detected | Not detected |
| | 10 days | Off-white solid | Crystal form C | 98.96 | 1.26 |

Conclusion: Influence factors and acceleration tests all showed that the crystal form C exhibits good thermal stability and stability under acceleration conditions.

Experimental Embodiment 4: Solid Stability Test of the Crystal Form D

A sample of the crystal form D was taken and placed on the bottom of a glass sample bottle, and spread to a thin layer. The sample stored under high temperature, high humidity, and acceleration conditions was placed in a bottle of which the mouth was packed with a pierced aluminum foil to ensure the sample to be sufficiently exposed to ambient air; the sample stored under light radiation conditions was placed at room temperature in a standing bottle of which the mouth was open, the sample was exposed to a light resource, and sampled for detection after being radiated by sufficient energy. Samples were taken and analyzed at various time points, and the test results were compared with the initial test results of 0 day. The inspection items included appearance, content and impurities; the test results are shown in Table 12.

TABLE 12

Solid Stability Test of Crystal Form D

| Conditions | Time Points | Appearance | Content (%) | Total Impurities (%) |
|---|---|---|---|---|
| — | 0 day | Off-white solid | 99.33 | 0.90 |
| High temperature (60° C., open) | 5 days | Off-white solid | Not detected | Not detected |
| | 10 days | Off-white solid | 99.32 | 0.94 |
| High humidity (room temperature/ relative humidity of 92.5%, open) | 5 days | Off-white solid | Not detected | Not detected |
| | 10 days | Off-white solid | 99.36 | 0.89 |
| Light radiation (total illumination: 1.2 × 10^6 Lux · hr/) | 5 days | Off-white solid | Not detected | Not detected |
| | 10 days | Off-white solid | 99.41 | 0.86 |
| Acceleration test (40° C./relative humidity of 75%, open) | 5 days | Off-white solid | Not detected | Not detected |
| | 10 days | Off-white solid | 99.38 | 0.96 |

Conclusion: Influence factors and acceleration tests all showed that the crystal form D exhibits good thermal stability, photostability, and stability under high humidity and acceleration conditions.

Experimental Embodiment 5: Solid Stability Test of the Crystal Form E

A sample of the crystal form E (10 mg) was taken and placed on the bottom of a glass sample bottle, and spread to a thin layer. The sample stored under high temperature, high humidity, and acceleration conditions was placed in a bottle of which the mouth was packed with a pierced aluminum foil to ensure the sample to be sufficiently exposed to ambient air; the sample stored under light radiation conditions was placed at room temperature in a standing bottle of which the mouth was open, the sample was exposed to a light resource, and sampled for detection after being radiated by sufficient energy, the control sample stored in dark (open, the whole sample bottle was sealed with aluminum foil to keep the content in dark) and the sample stored under light radiation conditions were placed together to exclude environmental influence on the samples. Samples were taken and analyzed at various time points, and the test results were compared with the initial test results of 0 day, the inspection items included appearance, crystal form, content and impurities, the test results are shown in Table 13.

TABLE 13

Solid Stability Test of Crystal Form E

| Conditions | Time Points | Appearance | Crystal Form (XRPD) | Content (%) | Total Impurities (%) |
|---|---|---|---|---|---|
| — | 0 day | White powder | Crystal form E | 101.51 | 0.44 |
| High temperature (60° C., open) | 5 days | White powder | Crystal form E | Not detected | Not detected |
| | 10 days | White powder | Crystal form E | 100.37 | 0.50 |
| High humidity (room temperature/ relative humidity of 92.5%, open) | 5 days | White powder | Crystal form E | Not detected | Not detected |
| | 10 days | White powder | Crystal form E | 101.24 | 0.34 |
| Light radiation (total illumination: $1.2 \times 10^6$ Lux · hr/near ultraviolet: 200 w · hr/m², open) | Light radiation | White powder | Crystal form E | 98.70 | 0.49 |
| | In dark | White powder | Crystal form E | 100.87 | 0.37 |
| Acceleration test (40° C./relative humidity of 75%, open) | 10 days | White powder | Crystal form E | 99.58 | 0.35 |
| | 1 month | White powder | Crystal form E | 102.95 | 0.33 |
| Acceleration test (60° C./relative humidity of 75%, open) | 10 days | White powder | Crystal form E | 100.38 | 0.37 |
| | 1 month | White powder | Crystal form E | 102.48 | 0.40 |

Conclusion: Influence factors and acceleration tests all showed that the crystal form E exhibits superior thermal stability and stability under acceleration conditions, and exhibits slight impurity generation under light radiation conditions, and good stability in dark.

Experimental Embodiment 6: Solid Stability Test of Crystal Form F

A sample of the crystal form F (10 mg) was placed on the bottom of a glass sample bottle, and spread to a thin layer. The sample stored under high temperature, high humidity, and acceleration conditions was placed in a bottle of which the mouth was packed with a pierced aluminum foil to ensure the sample to be sufficiently exposed to ambient air; the sample stored under light radiation conditions was placed at room temperature in a standing bottle of which the mouth was open, the sample was exposed to a light resource, and sampled for detection after being radiated by sufficient energy. Samples were taken and analyzed at various time points, and the test results were compared with the initial test results of 0 day, the inspection items included appearance, crystal form, content and impurities, the test results are shown in Table 14.

TABLE 14

Solid Stability Test of Crystal Form F

| Conditions | Time Points | Appearance | Crystal form (XRPD) | Content (%) | Total Impurities (%) |
|---|---|---|---|---|---|
| — | 0 day | White powder | Crystal form F | 99.26 | 0.72 |
| High temperature (60° C., open) | 5 days | White powder | Not detected | Not detected | Not detected |
| | 10 days | White powder | Crystal form F | 99.22 | 0.79 |
| High humidity (room temperature/ relative humidity of 92.5%, open) | 5 days | White powder | Not detected | Not detected | Not detected |
| | 10 days | White powder | Crystal form F | 99.24 | 0.73 |
| Light radiation (total illumination: $1.2 \times 10^6$ Lux · hr/) | 5 days | White powder | Not detected | Not detected | Not detected |
| | 10 days | White powder | Crystal form F | 99.30 | 0.73 |
| Acceleration test (40° C./relative humidity of 75%, open) | 5 days | White powder | Not detected | Not detected | Not detected |
| | 10 days | White powder | Crystal form F | 99.22 | 0.71 |

Conclusion: Influence factors and acceleration tests all show that the crystal form F exhibits good stabilities under high humidity and light radiation conditions and under acceleration conditions, and exhibits slight impurity generation at high temperature.

Experimental Embodiment 7: Solubility of the Crystal Form B, the Crystal Form E and the Crystal Form G in Various Biological Media Step 1: Preparation of Control Solutions (0.2 mg/mL, calculated by free base)

2 mg the crystal form B of the compound represented by formula (I) (or 2.4 mg the crystal form E of the compound represented by formula (II)) as a control was precisely weighed and placed into a 40 mL glass vial, and a diluent (10 mL) was precisely added. The reaction solution was subjected to ultrasonic treatment for 20 min to sufficiently dissolve, then cooled to room temperature and shaked well. Two control solutions (STD #1, STD #2) were formulated in accordance with this method.

Step 2: Preparation of Linear Solutions

The control solution STD #1 of the crystal form B of the compound represented by formula (I) was 1×, 10×, 100×, 1000× and 2000× (free base LOQ) diluted, and designated as the linear solutions L1, L2, L3, L4 and L5; the control solution STD #1 of the crystal form E of the compound represented by formula (II) was 1×, 10×, 100× and 1000× (methanesulfonate LOQ) diluted, and designated as the linear solutions L1, L2, L3, L4.

Step 3: Solubility Test of the crystal form B of the compound represented by formula (I), the crystal form G of the compound represented by formula (III) and the crystal form E of the compound represented by formula (II) in biological media and water 4 samples (about 4 mg) of each of the crystal form B of the compound represented by formula (I), the crystal form E of the compound represented by formula (II), and the crystal form G of the compound represented by formula (III) were added into 12 glass vials (4 mL), respectively, and then 2 mL different biological media (FaSSIF, FeSSIF, SGF) and water were added into each compound respectively, then mixed homogeneously to form a suspension. The suspension was detected for its initial pH value. A magnet was added into the suspension, and placed on a magnetic stirring heater for stirring (at a temperature of 37° C., in dark). After stirring for 24 h, a sample was taken. The taken sample was quickly centrifuged, and the residual solid was detected by XRPD. The supernatant was detected for its pH value and diluted with a diluent into appropriate multiple, then measured with HPLC for its concentration.

TABLE 15

Solubility Test Results in Various Biological Media (37° C.)

| Compounds | Biological Media | pH 0 hour | pH 24 hours | Status (24 h) | Solubility (mg/mL) 24 hours |
|---|---|---|---|---|---|
| Crystal form B of the | FaSSIF | 7.04 | 7.10 | Suspension | 0.041 |
| compound | FeSSIF | 4.98 | 5.18 | Suspension | 0.284 |
| represented by | SGF | 2.21 | 2.48 | Suspension | 0.014 |
| formula (I) | Water | 8.34 | 7.30 | Suspension | 0.007 |
| Crystal form E of the | Fassif | 6.97 | 6.81 | Suspension | 0.036 |
| compound | Fessif | 4.92 | 5.11 | Suspension | 0.358 |
| represented by | SGF | 2.17 | 2.31 | Suspension | 0.041 |
| formula (II) | Water | 3.50 | 2.74 | Suspension | 0.100 |
| Crystal form G of the | Fassif | 6.54 | 6.38 | Suspension | 0.079 |
| compound | Fessif | 4.87 | 4.99 | Suspension | 0.668 |
| represented by | SGF | 2.03 | 2.14 | Suspension | 0.045 |
| formula (III) | Water | 2.34 | 2.47 | Suspension | 0.028 |
| Standard curve | y = 34042x, r = 1 | | | | |
| LOQ | LOQ = 0.0001 mg/mL, S/N = 22.1 | | | | |

NOTE:
The results of the solubility of the compounds in salt form have been converted to the salt concentrations (the concentration was calculated based on the linear solution of the free base).

FaSSIF: 1. 0.042 g sodium hydroxide, 0.3438 g sodium dihydrogen phosphate and 0.6186 g sodium chloride were weighed, added into 90 mL purified water, and homogeneously mixed, then, the mixture was adjusted with 1 N hydrochloric acid or 1 N sodium hydroxide to pH=6.5, and diluted into a constant volume of 100 mL with purified water; 2. 50 mL of the buffer described above was taken, and 0.224 g commercially available powder (Biorelevant.com) of FaSSIF/FeSSIF/FaSSGF was added thereto, the mixture was stirred to dissolve, and diluted with purified water to a constant volume of 100 mL. The formulated buffer stood at room temperature for 2 hours, and was ready for use if the buffer was observed to be slightly milk white.

FeSSIF: 1. 0.404 g sodium hydroxide, 0.865 g glacial acetic acid, and 1.1874 g sodium chloride were weighed, added into 90 mL purified water, and homogeneously mixed, then, the mixture was adjusted with 1 N hydrochloric acid or 1 N sodium hydroxide to pH=5.0, and diluted with purified water to a constant volume of 100 mL, 2. 50 mL of the buffer described above was taken, and 1.12 g commercially available powder (Biorelevant.com) of FaSSIF/FeSSIF/FaSSGF was added thereto, the mixture was stirred to dissolve, and diluted with purified water to a constant volume of 100 mL. The formulated buffer stood at room temperature for 2 hours, and was ready for use if the buffer was observed to be clear liquid.

FaSSGF (SGF): 1. 0.2 g sodium chloride was weighed, added into 90 mL purified water, and mixed homogeneously, the mixture was adjusted with 1 N hydrochloric acid to pH=1.8, and diluted with purified water to a constant volume of 100 mL, and stood at room temperature.

LOQ: limit of quantitation.

Conclusion: The crystal form B of the compound represented by formula (I), the crystal form G of the compound represented by formula (III), and the crystal form E of the compound represented by formula (II) all exhibit good solubility in three types of biological media.

Experimental Embodiment 8: In Vitro Enzyme Activity Test

Experimental Objective

The enzyme activity was detected by Z'-LYTE® Assay with $IC_{50}$ value of the compound used as an index for evaluating the inhibitory effect of the compound on FGFR4 kinases. The activity test was completed in Life technology.

Experimental Method

The test compound was subjected to 3× gradient dilution, and the final concentrations included 10 concentrations from 10 μM to 0.5 nM, with two duplicates per concentration; the content of DMSO used in the detection reaction was 1%.

FGFR4 Enzymatic Reaction 1.94-84 ng FGFR1 protein kinase, 2 μM Tyr4 substrate, 150 μM ATP, 50 mM HEPES (pH 7.5), 0.01% BRIJ-35, 10 mM $MgCl_2$, 2 mM $MnCl_2$, 1 mM EGTA, 1 mM DTT. The detection plate was Bar-coded Corning, low volume NBS, black 384-well plate, the reaction was implemented at room temperature for 60 min, and the reaction system was 10 μL.

FGFR1 Enzymatic Reaction:

1 nM FGFR1 protein kinase, 2 μM Tyr4 peptide, 25 uM ATP, 50 mM HEPES (pH 7.5), 10 mM $MgCl_2$, 1 mM EGTA, 0.01% BRIJ-35, 2 mM $MnCl_2$, and 1 mM DTT. The detection plate was Black Proxiplate 384-Plus plate (PerkinElmer), the reaction was implemented at room temperature for 60 min, and the reaction system was 10 μL.

Reaction Detection:

5 μL Development reagent B (1:64) was added into the kinase reaction solution to stop the reaction, and the reaction solution was incubated at 23° C. for 60 min, the plate was read with Envision instrument.

Data Analysis

The data were converted to the phosphorylation rate and the inhibitory rate, and was subjected to curve fitting with Model 205 in XLFIT (iDBS) to give the $IC_{50}$ data of the compound. If the bottom of the curve was not in the range of −20% to 20%, it was set as 0%; and if the top of the curve was not in the range of 70% to 130%, it was set as 100%.

TABLE 16

$IC_{50}$ Test Results of Z'-LYTE ™ Detection (nM)

| Samples | FGFR4 $IC_{50}$ (nM) | FGFR1 $IC_{50}$ (nM) |
|---|---|---|
| Compound represented by formula (I) | 17 | 1,460.0 |

Conclusion: The core structure including acrylamide and fluoroolefin bond of the present disclosure can result in a series of highly FGFR4-selective compounds, which has excellent inhibitory activity on FGFR4 kinase, and have no activity on the subtype of FGFR1 kinase, the selectivity is at least 10 times or even more than 100 times.

What is claimed is:

1. A crystal form A, B, C or D of the compound represented by formula (I),

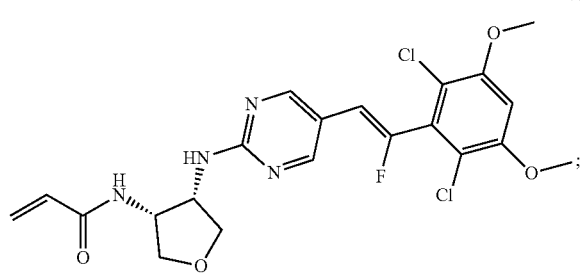

wherein (i) the X-ray powder diffraction pattern of the crystal form A has characteristic diffraction peaks at the following 2θ angles: 5.58±0.2°, 12.43±0.2°, 14.56±0.2°, 18.47±0.2°, 20.23±0.2°, 21.31±0.2°, 22.97±0.2°, 25.44±0.2°;

(ii) the X-ray powder diffraction pattern of the crystal form B has characteristic diffraction peaks at the following 2θ angles: 9.27±0.2°, 12.59±0.2°, 15.21±0.2°, 15.98±0.2°, 18.47±0.2°, 20.90±0.2°, 21.78±0.2°, 27.69±0.2°;

(iii) the X-ray powder diffraction pattern of the crystal form C has characteristic diffraction peaks at the following 2θ angles: 4.35±0.2°, 8.38±0.2°, 10.50±0.2°, 12.25±0.2°, 12.82±0.2°, 13.45±0.2°, 16.36±0.2°, 18.65±0.2°; and (iv) the X-ray powder diffraction pattern of the crystal form D has characteristic diffraction peaks at the following 2θ angles: 5.68±0.2°, 12.53±0.2°, 14.68±0.2°, 18.55±0.2°, 20.33±0.2°, 21.41±0.2°, 23.05±0.2°, 25.52±0.2°.

2. The crystal form A, B, C or D of the compound represented by formula (I) as defined in claim 1, wherein (i) the analytical data of the XRPD pattern of the crystal form A are as shown in the table below:

| Number | 2θ Angle (°) | Relative Intensity (%) |
|---|---|---|
| 1 | 5.583 | 7.9 |
| 2 | 10.946 | 7.6 |
| 3 | 11.512 | 5.1 |
| 4 | 12.427 | 21.3 |
| 5 | 12.765 | 24.5 |
| 6 | 13 | 46 |
| 7 | 14.562 | 10.2 |
| 8 | 15.691 | 5.1 |
| 9 | 16.66 | 7.5 |
| 10 | 17.96 | 6.7 |
| 11 | 18.47 | 24.3 |
| 12 | 19.598 | 6 |
| 13 | 20.229 | 29 |
| 14 | 20.999 | 13.2 |
| 15 | 21.311 | 47.9 |
| 16 | 22.44 | 13 |
| 17 | 22.973 | 100 |
| 18 | 24.864 | 16.5 |
| 19 | 25.438 | 59.4 |
| 20 | 27.136 | 12.5 |
| 21 | 27.607 | 8.4 |
| 22 | 27.871 | 6.1 |
| 23 | 28.818 | 7.3 |
| 24 | 29.447 | 5.9 |
| 25 | 31.343 | 3.8 |
| 26 | 31.788 | 3.9 |
| 27 | 32.247 | 4.3 |
| 28 | 32.584 | 11.3; |

(ii) the analytical data of the XRPD pattern of the crystal form B are as shown in the table below:

| Number | 2θ Angle (°) | Relative Intensity (%) |
|---|---|---|
| 1 | 6.149 | 7.6 |
| 2 | 7.044 | 2.2 |
| 3 | 9.272 | 66.2 |
| 4 | 12.115 | 13 |
| 5 | 12.587 | 100 |
| 6 | 13.97 | 7 |
| 7 | 15.212 | 9.3 |
| 8 | 15.982 | 21.4 |
| 9 | 18.468 | 15.3 |
| 10 | 19.383 | 5.4 |
| 11 | 19.713 | 9.9 |
| 12 | 20.01 | 5.7 |
| 13 | 20.9 | 56.3 |
| 14 | 21.508 | 9.3 |
| 15 | 21.785 | 33.2 |
| 16 | 22.302 | 5.1 |
| 17 | 22.596 | 12.7 |
| 18 | 22.853 | 11.1 |
| 19 | 23.404 | 7 |
| 20 | 24.156 | 26.6 |
| 21 | 24.394 | 28.7 |
| 22 | 24.685 | 8.4 |
| 23 | 25.182 | 7.4 |
| 24 | 26.365 | 8.6 |
| 25 | 27.693 | 24.1 |
| 26 | 28.777 | 6.8 |
| 27 | 29.856 | 3.2 |
| 28 | 31.482 | 5.4 |
| 29 | 32.096 | 1.4 |
| 30 | 33.435 | 7.4 |
| 31 | 35.627 | 3.4 |
| 32 | 36.515 | 4.3 |
| 33 | 37.027 | 5.5 |
| 34 | 38.018 | 4.3; |

(iii) the analytical data of the XRPD pattern of the crystal form C is as shown in the table below:

| Number | 2θ Angle (°) | Relative Intensity (%) |
|---|---|---|
| 1 | 4.352 | 13.6 |
| 2 | 8.378 | 15.3 |
| 3 | 10.496 | 25.7 |
| 4 | 11.838 | 72.1 |
| 5 | 12.253 | 100 |
| 6 | 12.824 | 29.9 |
| 7 | 13.453 | 18.3 |
| 8 | 14.131 | 7.7 |
| 9 | 16.359 | 15.1 |
| 10 | 16.637 | 11 |
| 11 | 17.047 | 19.9 |
| 12 | 17.685 | 8.5 |
| 13 | 17.92 | 13 |
| 14 | 18.647 | 28.2 |
| 15 | 19.006 | 4.4 |

-continued

| Number | 2θ Angle (°) | Relative Intensity (%) |
|---|---|---|
| 16 | 19.419 | 6.8 |
| 17 | 19.789 | 12 |
| 18 | 20.207 | 26.6 |
| 19 | 20.522 | 33.9 |
| 20 | 20.979 | 9.2 |
| 21 | 21.194 | 17 |
| 22 | 21.628 | 6 |
| 23 | 22.181 | 14.2 |
| 24 | 22.578 | 3.2 |
| 25 | 23.231 | 10 |
| 26 | 23.838 | 22.9 |
| 27 | 24.65 | 21.2 |
| 28 | 24.984 | 10.5 |
| 29 | 25.673 | 16.2 |
| 30 | 26.169 | 19.1 |
| 31 | 26.465 | 9.5 |
| 32 | 27.158 | 5.5 |
| 33 | 27.602 | 4.6 |
| 34 | 28.025 | 9.4 |
| 35 | 28.679 | 11.5 |
| 36 | 28.914 | 13.3 |
| 37 | 30.629 | 5.3 |
| 38 | 31.052 | 8.5 |
| 39 | 32.705 | 5.7 |
| 40 | 35.821 | 10.3 | and (iv) the analytical data of the XRPD pattern of the crystal form D is as shown in the table below:

| Number | 2θ Angle (°) | Relative Intensity (%) |
|---|---|---|
| 1 | 5.679 | 11.7 |
| 2 | 11.008 | 9.5 |
| 3 | 11.559 | 4.8 |
| 4 | 12.527 | 31.8 |
| 5 | 12.864 | 32.4 |
| 6 | 13.061 | 53.2 |
| 7 | 14.679 | 14.5 |
| 8 | 15.786 | 6 |
| 9 | 16.809 | 10.3 |
| 10 | 18.076 | 9.2 |
| 11 | 18.549 | 32.7 |
| 12 | 19.657 | 6.5 |
| 13 | 20.325 | 37 |
| 14 | 20.979 | 18.3 |
| 15 | 21.409 | 55.2 |
| 16 | 22.281 | 5.4 |
| 17 | 22.575 | 19 |
| 18 | 23.049 | 100 |
| 19 | 24.964 | 22.4 |
| 20 | 25.517 | 67.4 |
| 21 | 26.097 | 3.6 |
| 22 | 26.41 | 4.6 |
| 23 | 27.254 | 19.1 |
| 24 | 27.65 | 8.9 |
| 25 | 27.981 | 7.5 |
| 26 | 28.895 | 9.7 |
| 27 | 29.544 | 7 |
| 28 | 31.775 | 5.6 |
| 29 | 32.643 | 16 |
| 30 | 33.692 | 5.7 |
| 31 | 34.383 | 4.3 |
| 32 | 34.737 | 5.5 |
| 33 | 36.87 | 5.3 |
| 34 | 37.936 | 5.6 |
| 35 | 38.601 | 4.6. |

3. The crystal form A, B, C or D of the compound represented by formula (I) as defined in claim 2, wherein (i) the XRPD pattern of the crystal form A is as shown in FIG. 1;
  (ii) the XRPD pattern of the crystal form B is as shown in FIG. 4;
  (iii) the XRPD pattern of the crystal form C is as shown in FIG. 7; and
  (iv) the XRPD pattern of the crystal form D is as shown in FIG. 10.

4. The crystal form A, B, C or D of the compound represented by formula (I) as defined in claim 1, wherein (i) the differential scanning calorimetric curve of the crystal form A has an endothermic peak with an onset of 174.46° C.±3° C.;
  (ii) the differential scanning calorimetric curve of the crystal form B has an endothermic peak with an onset of 178.04° C.±3° C.;
  (iii) the differential scanning calorimetric curve of the crystal form C has an endothermic peak with an onset of 179.19° C.±3° C.; and
  (iv) the differential scanning calorimetric curve of the crystal form D has an endothermic peak with an onset of 179.17° C.±3° C.

5. The crystal form A, B, C or D of the compound represented by formula (I) as defined in claim 4, wherein
  (i) the DSC pattern of the crystal form A is as shown in FIG. 2;
  (ii) the DSC pattern of the crystal form B is as shown in FIG. 5;
  (iii) the DSC pattern of the crystal form C is as shown in FIG. 8; and
  (iv) the DSC pattern of the crystal form D is as shown in FIG. 11.

6. The crystal form A, B, C or D of the compound represented by formula (I) as defined in claim 1, wherein the thermogravimetric analysis curve of the crystal form A has a weight loss of 0.02335% occurred at 120.00° C.±3° C., and an additional weight loss of 0.2869% occurred at 200.85° C.±3° C.;
  (ii) the thermogravimetric analysis curve of the crystal form B has a weight loss of 0.8093% occurred at 120.00° C.±3° C., and an additional weight loss of 1.128% occurred at 200.04° C.±3° C.;
  (iii) the thermogravimetric analysis curve of the crystal form C has a weight loss of 0.4101% occurred at 120.00° C.±3° C., and an additional weight loss of 0.2938% occurred at 200.31° C.±3° C.; and
  (iv) the thermogravimetric analysis curve of the crystal form D has a weight loss of 0.6366% occurred at 196.80° C.±3° C.

7. The crystal form A, B, C or D of the compound represented by formula (I) as defined in claim 6, wherein
  (i) the TGA pattern of the crystal form A is as shown in FIG. 3;
  (ii) the TGA pattern of the crystal form B is as shown in FIG. 6;
  (iii) the TGA pattern of the crystal form C is as shown in FIG. 9; and
  (iv) the TGA pattern of the crystal form D is as shown in FIG. 12.

8. A method for preparing a crystal form B of the compound represented by formula (I) as defined in claim 1, comprising preparing the crystal form B by adding the compound represented by formula (I) into a solvent, heating and stirring, or by carrying out recrystallization, wherein the solvent is selected from: methanol, ethanol, acetone, tetrahydrofuran, isopropanol or ethanol-water, the stirring temperature is 10° C. to 45° C., the time for slurrying with stirring is 10 hours to 60 hours, and the weight-volume ratio of the compound to the solvent is 1:8-15 g/mL.

9. The crystal form A, B, C or D of the compound represented by formula (I) as defined in claim 1, wherein (i) the X-ray powder diffraction pattern of the crystal form A has characteristic diffraction peaks at the following 2θ angles: 5.58±0.2°, 12.43±0.2°, 12.77±0.2°, 13.00±0.2°, 14.56±0.2°, 18.47±0.2°, 20.23±0.2°, 21.00±0.2°, 21.31±0.2°, 22.44±0.2°, 22.97±0.2°, 24.86±0.2°, 25.44±0.2°, 27.14±0.2°;

(ii) the X-ray powder diffraction pattern of the crystal form B has characteristic diffraction peaks at the following 2θ angles: 9.27±0.2°, 12.12±0.2°, 12.59±0.2°, 15.21±0.2°, 15.98±0.2°, 18.47±0.2°, 20.90±0.2°, 21.79±0.2°, 22.60±0.2°, 22.85±0.2°, 24.16±0.2°, 24.39±0.2°, 27.69±0.2°;

(iii) the X-ray powder diffraction pattern of the crystal form C has characteristic diffraction peaks at the following 2θ angles: 4.35±0.2°, 8.38±0.2°, 10.50±0.2°, 11.84±0.2°, 12.25±0.2°, 12.82±0.2°, 13.45±0.2°, 16.36±0.2°, 16.64±0.2°, 17.05±0.2°, 17.92±0.2°, 18.65±0.2°, 19.79±0.2°, 20.21±0.2°, 20.52±0.2°, 21.19±0.2°, 22.18±0.2°, 23.23±0.2°, 23.84±0.2°, 24.65±0.2°, 25.67±0.2°, 26.17±0.2°, 28.91±0.2°; and (iv) the X-ray powder diffraction pattern of the crystal form D has characteristic diffraction peaks at the following 2θ angles: 5.68±0.2°, 12.53±0.2°, 13.06±0.2°, 14.68±0.2°, 16.81±0.2°, 18.55±0.2°, 20.33±0.2°, 20.98±0.2°, 21.41±0.2°, 22.58±0.2°, 23.05±0.2°, 24.96±0.2°, 25.52±0.2°, 27.25±0.2°.

10. A method for treating FGFR4 related disease in a subject in need thereof, comprising administering an effective amount of the crystal form A, B, C or D of the compound represented by formula (I) as defined in claim 1 to the subject.

11. A compound represented by formula (II) or crystal form E or F thereof,

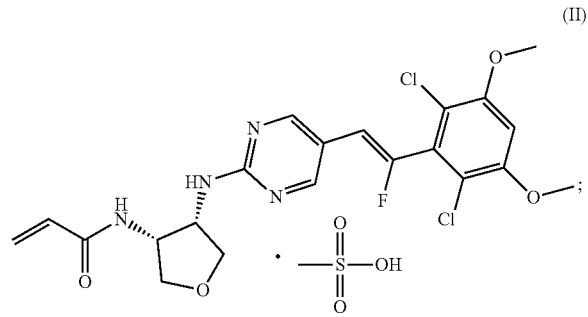

(II)

wherein the X-ray powder diffraction pattern of the crystal form E has characteristic diffraction peaks at the following 2θ angles: 5.95±0.2°, 11.77±0.2°, 12.53±0.2°, 18.53±0.2°, 19.28±0.2°, 21.12±0.2°, 22.42±0.2°, 25.76±0.2°; and the X-ray powder diffraction pattern of the crystal form F has characteristic diffraction peaks at the following 2θ angles: 6.04±0.2°, 9.21±0.2°, 12.02±0.2°, 12.51±0.2°, 15.88±0.2°, 18.35±0.2°, 20.84±0.2°, 21.67±0.2°.

12. The compound represented by formula (II) or crystal form E or F thereof as defined in claim 11, wherein (i) the analytical data of the XRPD pattern of the crystal form E is as shown in the table below:

| Number | 2θ Angle (°) | Relative Intensity (%) |
|---|---|---|
| 1 | 5.95 | 48.3 |
| 2 | 10.752 | 3.8 |
| 3 | 11.772 | 42.8 |
| 4 | 11.978 | 19.5 |
| 5 | 12.529 | 36.9 |
| 6 | 17.599 | 4.1 |
| 7 | 18.528 | 27.8 |
| 8 | 19.281 | 27.1 |
| 9 | 20.111 | 6.6 |
| 10 | 20.445 | 4.2 |
| 11 | 20.781 | 24 |
| 12 | 21.115 | 59.7 |
| 13 | 21.495 | 20.7 |
| 14 | 21.985 | 15.5 |
| 15 | 22.418 | 100 |
| 16 | 23.01 | 18.4 |
| 17 | 23.942 | 18.6 |
| 18 | 24.353 | 33 |
| 19 | 25.063 | 15.2 |
| 20 | 25.303 | 6.9 |
| 21 | 25.756 | 29.2 |
| 22 | 26.073 | 7.1 |
| 23 | 26.368 | 9 |
| 24 | 26.681 | 11 |
| 25 | 27.116 | 14.4 |
| 26 | 28.653 | 8.7 |
| 27 | 29.423 | 2.4 |
| 28 | 30.023 | 11.4 |
| 29 | 30.828 | 10.6 |
| 30 | 31.341 | 17.4 |
| 31 | 31.933 | 9 |
| 32 | 32.464 | 6.4 |
| 33 | 32.841 | 4.7 |
| 34 | 33.315 | 4.9 |
| 35 | 34.974 | 27.3 |
| 36 | 37.639 | 7.6. | and
(ii) the analytical data of the XRPD pattern of the crystal form F is as shown in the table below:

| Number | 2θ Angle (°) | Relative Intensity (%) |
|---|---|---|
| 1 | 6.036 | 19.8 |
| 2 | 9.209 | 100 |
| 3 | 12.017 | 17 |
| 4 | 12.509 | 98.6 |
| 5 | 13.889 | 7.9 |
| 6 | 15.114 | 9.1 |
| 7 | 15.885 | 22.1 |
| 8 | 18.352 | 15.2 |
| 9 | 19.286 | 4 |
| 10 | 19.71 | 12.6 |
| 11 | 20.027 | 7.2 |
| 12 | 20.839 | 51.1 |
| 13 | 21.669 | 32.7 |
| 14 | 22.324 | 5.9 |
| 15 | 22.594 | 14.7 |
| 16 | 23.348 | 7.6 |
| 17 | 24.136 | 28.5 |
| 18 | 24.647 | 9.3 |
| 19 | 25.048 | 4.5 |
| 20 | 26.288 | 7.3 |
| 21 | 27.136 | 4 |
| 22 | 27.649 | 18.3 |
| 23 | 28.481 | 4.1 |
| 24 | 28.831 | 6.2 |
| 25 | 29.781 | 3.2 |
| 26 | 31.479 | 4.9 |
| 27 | 33.354 | 5.9 |
| 28 | 33.588 | 4.8 |
| 29 | 36.511 | 4.7 |

-continued

| Number | 2θ Angle (°) | Relative Intensity (%) |
|---|---|---|
| 30 | 36.944 | 4.2 |
| 31 | 37.953 | 2.8. |

13. The compound represented by formula (II) or crystal form E or F thereof as defined in claim 12, wherein (i) the XRPD pattern of the crystal form E is as shown in FIG. 13; and
  (ii) the XRPD pattern of the crystal form F is as shown in FIG. 16.

14. The compound represented by formula (II) or crystal form E or F thereof as defined in claim 11, wherein (i) the differential scanning calorimetric curve of the crystal form E has an endothermic peak with an onset of 193.78° C.±3° C. and an exothermic peak at 198.70° C.±3° C.; and
  (ii) the differential scanning calorimetric curve of the crystal form F has an endothermic peak with an onset of 155.72° C.±3° C.

15. The compound represented by formula (II) or crystal form E or F thereof as defined in claim 14, wherein
  (i) the DSC pattern of the crystal form E is as shown in FIG. 14; and
  (ii) the DSC pattern of the crystal form F is as shown in FIG. 17.

16. The compound represented by formula (II) or crystal form E or F thereof as defined in claim 11, wherein (i) the thermogravimetric analysis curve of the crystal form E has a weight loss of 1.086% occurred at 170.64° C.±3° C., and an additional weight loss of 1.652% occurred at 210.29° C.±3° C.; and
  (ii) the thermogravimetric analysis curve of the crystal form F has a weight loss of 0.6525% occurred at 120° C.±3° C., and an additional weight loss of 1.138% occurred at 205.16° C.±3° C.

17. The compound represented by formula (II) or crystal form E or F thereof as defined in claim 16, wherein (i) the TGA pattern of the crystal form E is as shown in FIG. 15; and
  (ii) the TGA pattern of the crystal form F is as shown in FIG. 18.

18. The compound represented by formula (II) or crystal form E or F thereof as defined in claim 11, wherein the X-ray powder diffraction pattern of the crystal form E has characteristic diffraction peaks at the following 2θ angles: 5.95±0.2°, 11.77±0.2°, 11.98±0.2°, 12.53±0.2°, 18.53±0.2°, 19.28±0.2°, 20.78±0.2°, 21.12±0.2°, 21.50±0.2°, 21.99±0.2°, 22.42±0.2°, 23.01±0.2°, 23.94±0.2°, 24.35±0.2°, 25.06±0.2°, 25.76±0.2°, 27.12±0.2°; and
  the X-ray powder diffraction pattern of the crystal form F has characteristic diffraction peaks at the following 2θ angles: 6.04±0.2°, 9.21±0.2°, 12.02±0.2°, 12.51±0.2°, 15.89±0.2°, 18.35±0.2°, 19.71±0.2°, 20.84±0.2°, 21.67±0.2°, 22.59±0.2°, 24.14±0.2°, 27.64±0.2°.

19. A method for treating FGFR4 related disease in a subject in need thereof, comprising administering an effective amount of the compound represented by formula (II) or crystal form E or F thereof as defined in claim 11 to the subject.

20. A compound represented by formula (III) or crystal form G thereof,

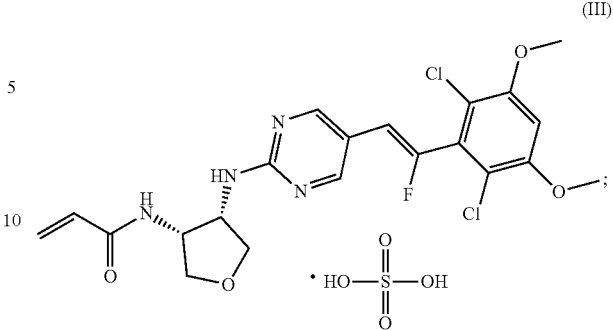

(III)

wherein the X-ray powder diffraction pattern of the crystal form G has characteristic diffraction peaks at the following 2θ angles: 5.86±0.2°, 11.62±0.2°, 12.31±0.2°, 19.22±0.2°, 20.03±0.2°, 22.81±0.2°, 23.68±0.2°, 24.75±0.2°.

21. The compound represented by formula (III) or crystal form G thereof as defined in claim 20, wherein the analytical data of the XRPD pattern of the crystal form G is as shown in the table below:

| Number | 2θ Angle (°) | Relative Intensity (%) |
|---|---|---|
| 1 | 5.857 | 30.6 |
| 2 | 10.558 | 6.1 |
| 3 | 11.624 | 37.4 |
| 4 | 12.31 | 22.8 |
| 5 | 19.22 | 33 |
| 6 | 20.028 | 26.3 |
| 7 | 20.839 | 43.6 |
| 8 | 21.175 | 22.3 |
| 9 | 21.63 | 14.4 |
| 10 | 22.186 | 4.7 |
| 11 | 22.812 | 100 |
| 12 | 23.682 | 30.6 |
| 13 | 24.746 | 53.3 |
| 14 | 25.175 | 6.6 |
| 15 | 26.229 | 26.9 |
| 16 | 26.821 | 17.5 |
| 17 | 27.333 | 5.5 |
| 18 | 28.968 | 8.5 |
| 19 | 29.168 | 4.5 |
| 20 | 30.298 | 10.6 |
| 21 | 30.612 | 9.1 |
| 22 | 31.599 | 17.2 |
| 23 | 31.868 | 6.9 |
| 24 | 32.707 | 3.6 |
| 25 | 35.15 | 19.5 |
| 26 | 37.897 | 5.3 |
| 27 | 38.823 | 7.9. |

22. The compound represented by formula (III) or crystal form G thereof as defined in claim 20, wherein the differential scanning calorimetric curve of the crystal form G has an endothermic peak with an onset of 164.93° C.±3° C.

23. The compound represented by formula (III) or crystal form G thereof as defined in claim 20, wherein the thermogravimetric analysis curve of the crystal form G has a weight loss of 0.2051% occurred at 120° C.±3° C., and an additional weight loss of 2.867% occurred at 218.92° C.±3° C.

24. A method for treating FGFR4 related disease in a subject in need thereof, comprising administering an effective amount of the compound represented by formula (III) or crystal form G thereof as defined in claim 20 to the subject.

25. The compound represented by formula (III) or crystal form G thereof as defined in claim 20, wherein the X-ray powder diffraction pattern of the crystal form G has characteristic diffraction peaks at the following 2θ angles: 5.86±0.2°, 11.62±0.2°, 12.31±0.2°, 19.22±0.2°, 20.03±0.2°, 20.84±0.2°, 21.18±0.2°, 21.63±0.2°, 22.81±0.2°, 23.68±0.2°, 24.75±0.2°, 26.23±0.2°, 26.82±0.2°.

26. The compound represented by formula (III) or crystal form G thereof as defined in claim 20, wherein the XRPD pattern of the crystal form G is as shown in FIG. 19;

the DSC curve of the crystal form G is as shown in FIG. 20; or the TGA pattern of the crystal form G is as shown in FIG. 21.

* * * * *